(12) United States Patent
Guo et al.

(10) Patent No.: US 10,663,465 B2
(45) Date of Patent: May 26, 2020

(54) DISRUPTION OF EGFR-SAR1 INTERACTION FOR CANCER TREATMENT

(71) Applicant: The Hong Kong University of Science and Technology, Kowloon (CN)

(72) Inventors: Yusong Guo, Clear Water Bay (CN); Pik Ki Lau, Yuen Long (CN); Yixin Lin, Clear Water Bay (CN)

(73) Assignee: The Hong Kong University of Science and Technology, Clear Water Bay (HK)

( * ) Notice: Subject to any disclaimer, the term of this patent is extended or adjusted under 35 U.S.C. 154(b) by 0 days.

(21) Appl. No.: 16/254,287

(22) Filed: Jan. 22, 2019

(65) Prior Publication Data
US 2019/0277844 A1 Sep. 12, 2019

Related U.S. Application Data

(60) Provisional application No. 62/710,869, filed on Mar. 5, 2018.

(51) Int. Cl.
| | | |
|---|---|---|
| *G01N 33/53* | (2006.01) | |
| *G01N 33/566* | (2006.01) | |
| *G01N 33/573* | (2006.01) | |
| *C12N 15/113* | (2010.01) | |
| *A61P 35/00* | (2006.01) | |
| *A61K 31/7088* | (2006.01) | |
| *A61K 9/00* | (2006.01) | |
| *A61K 31/713* | (2006.01) | |
| *G01N 33/574* | (2006.01) | |
| *G01N 33/50* | (2006.01) | |
| *G01N 33/68* | (2006.01) | |

(52) U.S. Cl.
CPC ......... *G01N 33/566* (2013.01); *A61K 9/0019* (2013.01); *A61K 31/7088* (2013.01); *A61K 31/713* (2013.01); *A61P 35/00* (2018.01); *C12N 15/1137* (2013.01); *C12N 15/1138* (2013.01); *G01N 33/5011* (2013.01); *G01N 33/573* (2013.01); *G01N 33/574* (2013.01); *G01N 33/6872* (2013.01); *C12N 2310/111* (2013.01); *C12N 2310/14* (2013.01); *C12N 2320/32* (2013.01); *G01N 2333/71* (2013.01); *G01N 2333/914* (2013.01); *G01N 2500/04* (2013.01)

(58) Field of Classification Search
None
See application file for complete search history.

(56) References Cited

PUBLICATIONS

Guo et al. (2014) Ann. Rev. Cell Dev. Biol. 30: 169-206.*

* cited by examiner

*Primary Examiner* — Michael D Pak
(74) *Attorney, Agent, or Firm* — Kilpatrick Townsend & Stockton LLP

(57) ABSTRACT

The present invention relates to the discovery that delivery of EGFR to cell surface requires EGFR-SAR1A binding. Thus, the invention provides a method for identifying inhibitors of EGFR-SAR1A binding, which can serve as therapeutic agents for treating conditions involving undesirable EGFR signaling. The invention also provides novel composition and its use that suppresses the specific binding between EGFR and SAR1A for the purpose of treating or preventing a condition involving undesired EGFR signaling.

15 Claims, 11 Drawing Sheets

Specification includes a Sequence Listing.

FIG. 2A  
EGFR-GFP
FIG. 2B  
SAR1A(H79G)-DsRed
FIG. 2C  
PDI
FIG. 2D  
EGFR / Sar1 / PDI
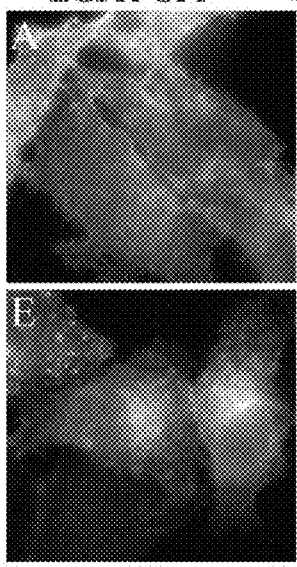 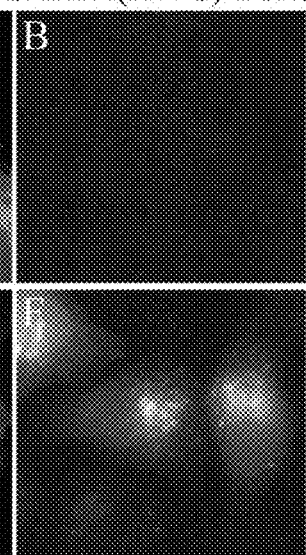 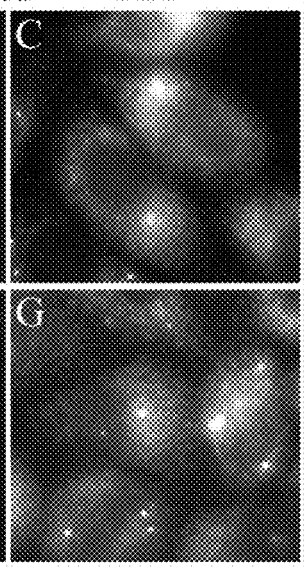 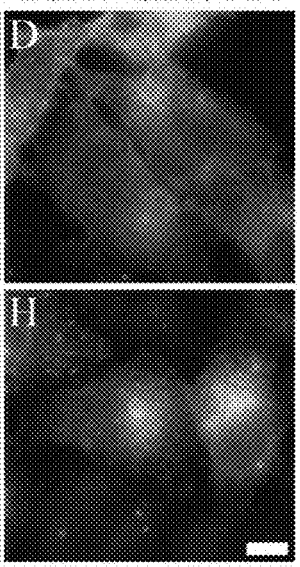
FIG. 2E
FIG. 2F
FIG. 2G
FIG. 2H FIGURES 4A-4B
FIGURE 4A
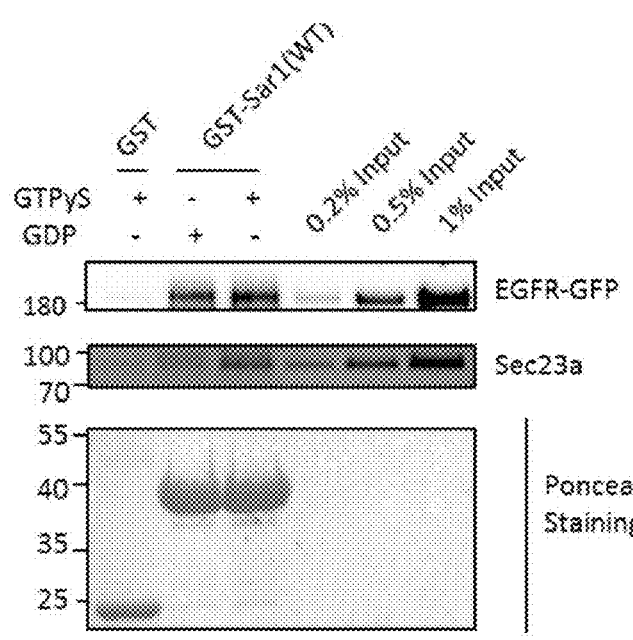
FIGURE 4B
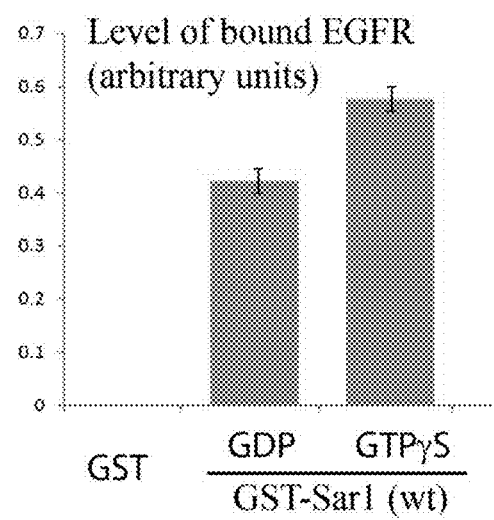

FIGURES 5A-5B
FIGURE 5A
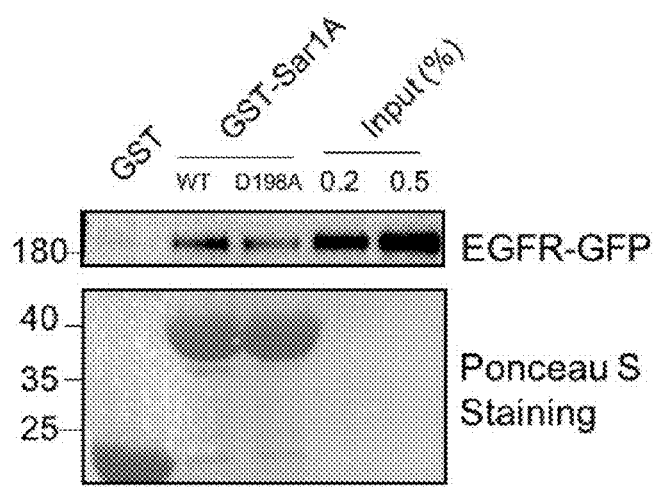
FIGURE 5B
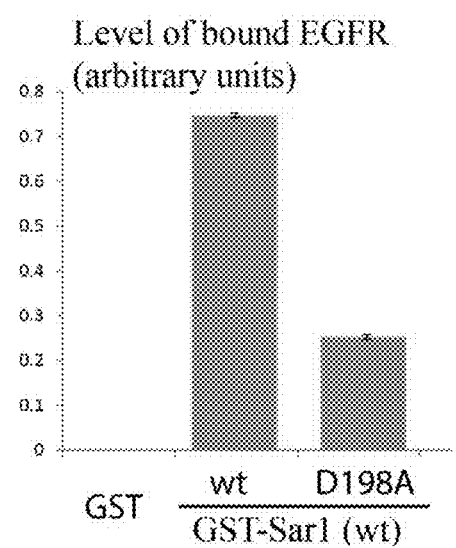

FIGURES 7A-7B
FIGURE 7A
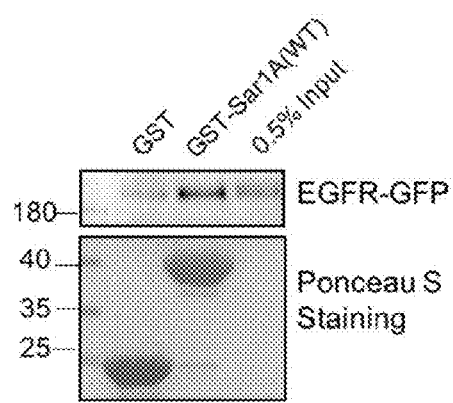
FIGURE 7B
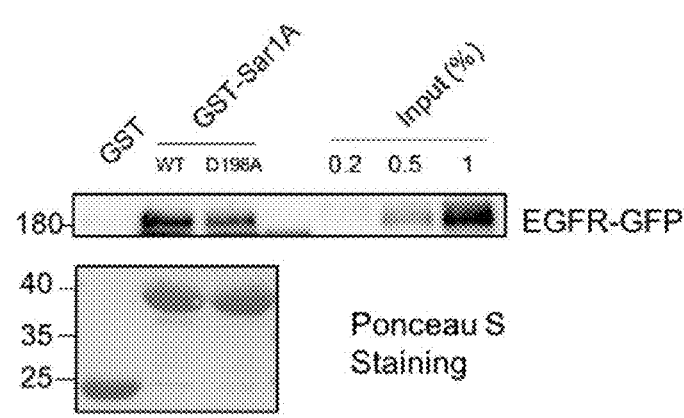

EGFR-GFP | SAR1A(wt)-DsRed | PDI | EGFR / SAR1A

EGFR-GFP | SAR1A(D198A)-DsRed | PDI | EGFR / SAR1A

FIGURES 9A-9F
FIGURE 9A FIGURE 9B FIGURE 9C
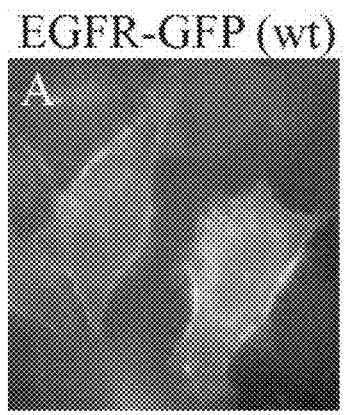 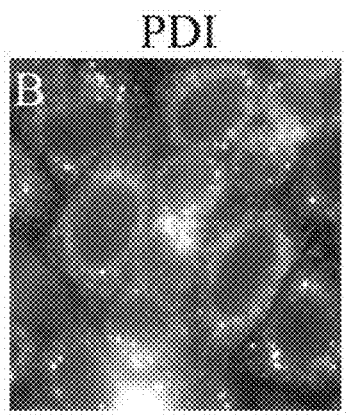 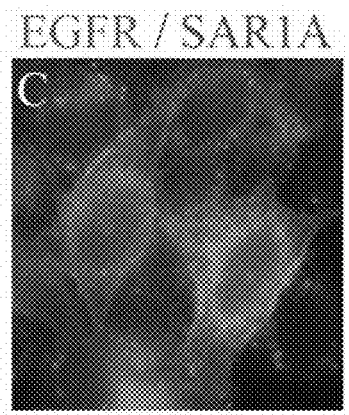
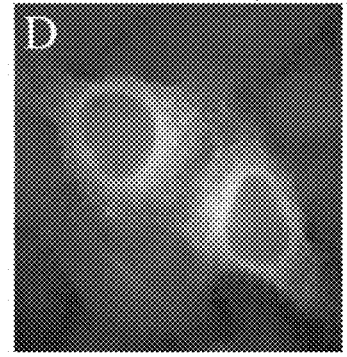 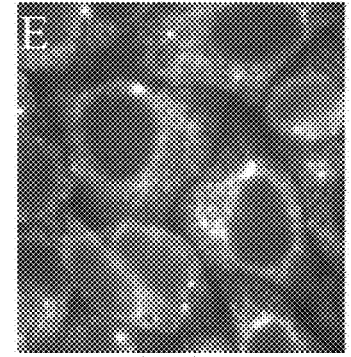 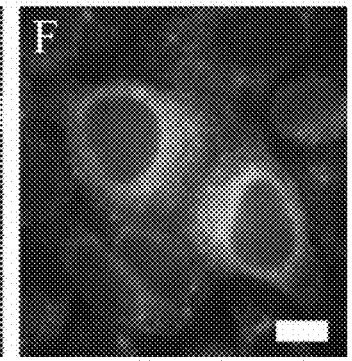
FIGURE 9D FIGURE 9E FIGURE 9F FIGURES 10A-10C
FIGURE 10A
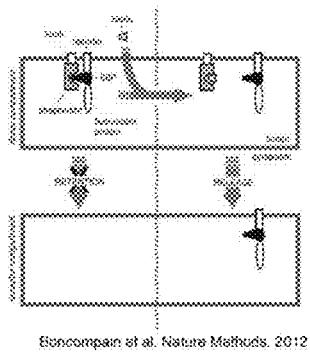
FIGURE 10B
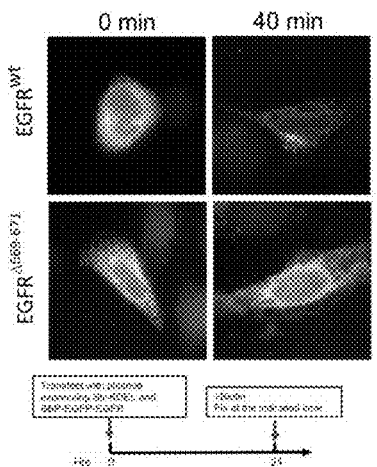
FIGURE 10C
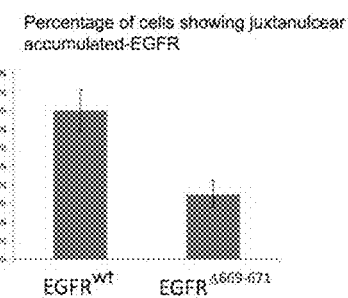

| FIGURE 11A | FIGURE 11B | FIGURE 11C | FIGURE 11D |
|---|---|---|---|
| EGFR-GFP | Sar1A(H79G)-DsRed | phospho-EGFR | EGFR/Sar1A/pEGFR |

| EGFR-GFP | Sar1A(H79G)-DsRed | phospho-EGFR | EGFR/Sar1A/pEGFR |
|---|---|---|---|

| FIGURE 11E | FIGURE 11F | FIGURE 11G | FIGURE 11H |
|---|---|---|---|

DISRUPTION OF EGFR-SAR1 INTERACTION FOR CANCER TREATMENT

RELATED APPLICATIONS

This application claims priority to U.S. Provisional Patent Application No. 62/710,869, filed on Mar. 5, 2018, the contents of which are hereby incorporated by reference in the entirety for all purposes.

REFERENCE TO SUBMISSION OF A SEQUENCE LISTING AS A TEXT FILE

The instant application contains a Sequence Listing which has been filed electronically in ASCII format and is hereby incorporated by reference in its entirety. Said ASCII copy, created on Mar. 29, 2019, is named 091256-1119719-001710US_SL.txt and is 24,394 bytes in size.

BACKGROUND OF THE INVENTION

The epidermal growth factor receptor (EGFR) is a transmembrane protein, a receptor for members of the epidermal growth factor family (EGF family) and other extracellular protein ligands. There are four closely related members of the EGFR family: EGFR (ErbB-1), HER2/neu (ErbB-2), Her 3 (ErbB-3) and Her 4 (ErbB-4), each being a receptor tyrosine kinase. EGFR is frequently overexpressed or mutated in majority of human cancers, such as cancers of the head and neck, breast, ovary, cervix, lung etc. As an example, EGFR is overexpressed in 62% of non-small cell lung cancer cases, and its expression is correlated with a poor prognosis. Overexpression of EGFR has also been reported in up to 40% of breast cancer cases and is known to correlate with poor clinical outcome. Further, many epithelial cancer cells contain mutations on EGFR that constitutively activate EGFR at expression or activity level and are thought to promote the occurrence, progression, and/or metastasis of cancer.

Due to its frequent and significant involvement in various human malignancies, EGFR has been a major target in cancer therapy. Currently available treatment strategies targeting EGFR involve the use of EGFR tyrosine kinase inhibitors and anti-EGFR antibodies. While varying degree of efficacy has been reported, cancer patients receiving the EGFR antagonist therapy tend to develop resistance to the treatment over time, which ultimately renders such treatment ineffective. Thus, there exists an urgent need to establish new and more effective therapeutic methods for treating conditions especially cancers where overexpression of EGFR or inappropriate activation of EGFR-mediated cellular signaling is a significant component. The present invention fulfills this and other related needs.

BRIEF SUMMARY OF THE INVENTION

In one aspect, the present invention provides a method for identifying an inhibitor for EGFR-SAR1A binding. The method comprises the steps of: (a) contacting a test compound with an EGFR polypeptide comprising the amino acid sequence set forth in SEQ ID NO:2 and an SAR1A polypeptide comprising the amino acid sequence set forth in SEQ ID NO:4, under conditions that permit specific binding between EGFR polypeptide and SAR1A polypeptide; and (b) determining the level of specific binding between the EGFR polypeptide and the SAR1A polypeptide, wherein a decrease in the level of specific binding compared to a control level of specific binding between the EGFR polypeptide and the SAR1A polypeptide under the same conditions but in the absence of the test compound indicates the compound as an inhibitor for EGFR-SAR1A binding.

In some embodiments, the EGFR polypeptide comprises the amino acid sequence set forth in SEQ ID NO:1 or 2. In some embodiments, the SAR1A polypeptide comprises the amino acid sequence set forth in SEQ ID NO:3 or 4. In some embodiments, the EGFR polypeptide is immobilized on a solid support. In some embodiments, the SAR1A polypeptide is immobilized on a solid support. In some embodiments, the EGFR polypeptide or the SAR1A polypeptide is labeled with a detectable label such as a radioactive label or a fluorescent dye. In some embodiments, one of the EGFR and SAR1A polypeptides is immobilized on a solid support whereas the other is labeled with a detectable label: for example, the EGFR polypeptide is immobilized to a solid support whereas the SAR1A polypeptide is labeled with a detectable label; or the SAR1A polypeptide is immobilized to a solid support whereas the EGFR polypeptide is labeled with a detectable label. In some embodiments, the EGFR polypeptide further comprises at least one heterologous amino acid sequence at the C- and/or N-terminus of the amino acid sequence set forth in SEQ ID NO:1 or 2. In some embodiments, the EGFR polypeptide consists of SEQ ID NO:1 or 2. In some embodiments, the SAR1A polypeptide further comprises at least one heterologous amino acid sequence at the C- and/or N-terminus of the amino acid sequence set forth in SEQ ID NO:3 or 4. In some embodiments, the SAR1A polypeptide consists of SEQ ID NO:3 or 4. In some embodiments, the method further comprises, after the compound has been identified as an inhibitor for EGFR-SAR1A binding, the steps of (i) exposing a cell expressing EGFR and SAR1A to an effective amount of the compound; and (ii) measuring EGFR-SAR1A binding level in the cell and comparing with EGFR-SAR1A binding level in the absence of the compound or measuring EGFR level on the cell surface and comparing with EGFR level on the cell surface in the absence of the compound.

In a second aspect, the prevent invention provides a method for treating a condition involving excessive or aberrant EGFR signaling. The method comprises the step of administering to a subject in need thereof an effective amount of an inhibitor for EGFR-SAR1A binding. In some embodiments, the inhibitor is an EGFR fragment (which is less than full-length EGFR) comprising or consisting of the amino acid sequence set forth in SEQ ID NO:2, optionally further comprising one or more heterologous amino acid sequence. In some embodiments, the inhibitor is an SAR1A fragment (which is less than full-length SAR1A) comprising or consisting of the amino acid sequence set forth in SEQ ID NO:4, optionally further comprising one or more heterologous amino acid sequence.

In some embodiments, the inhibitor is an antisense oligonucleotide, a small inhibitory RNA specifically inhibiting EGFR expression. In some embodiments, the inhibitor is an antisense oligonucleotide or a small inhibitory RNA specifically inhibiting SAR1A expression. In some embodiments, the inhibitor is administered by injection, such as intravenous injection, intraperitoneal injection, or intratumoral injection as in the case of treating a solid tumor that is EGFR$^+$. In some embodiments, the inhibitor is administered by inhalation such as by intranasal delivery as in the case of treating a chronic respiratory disease.

In a third aspect, the present invention provides a composition useful for treating a condition involving excessive or aberrant EGFR signaling. The composition comprises (1)

an effective amount of an inhibitor for EGFR-SAR1A binding and (2) a pharmaceutically acceptable carrier. In some embodiments, the inhibitor is an antisense oligonucleotide or a small inhibitory RNA specifically inhibiting EGFR expression. In some embodiments, the inhibitor is an antisense oligonucleotide or a small inhibitory RNA specifically inhibiting SAR1A expression. In some embodiments, the composition is formulated for injection or for nasal delivery. In some embodiments, the composition may further include an additional therapeutic compound (such as osimertinib and gefitinib) that is known to be effective for treating cancer or a chronic lung disease.

BRIEF DESCRIPTION OF THE DRAWINGS

FIGS. 2A-2H. Measurement of the effects of H79G mutation in SAR1A on surface localizations of EGFR. The small GTPase SAR1A is a key player in mediating COPII vesicle formation at the ER. Introducing H79G mutation in SAR1A locks SAR1A in its GTP-bound form and inhibits the COPII-dependent ER export process. HeLa cells were transfected with EGFR-GFP (FIG. 2A-D) or co-transfected with EGFR-GFP and SAR1A (H79G)-DsRed (FIG. 2E-H). Day 1 after transfection, the localizations of EGFR, Sar1A (H79G) and the ER marker, PDI, were analyzed by immunofluorescence. Size bar, 10 μm. It was observed that overexpressing of SAR1A (H79G)-DsRed in HeLa cells causes strong accumulations of EGFR at the ER (FIG. 2E-H). In contrast, EGFR is localized at the cell surface in HeLa cells not expressing SAR1A (H79G)-DsRed (FIG. 2A-D).

FIGS. 4A-4B. Measurement of the binding between SAR1A and EGFR. GST or GST-tagged SAR1A were purified from bacteria. COS7 cells were transfected with EGFR-GFP. Day1 after transfection, cells were lysed and the cell lysates containing EGFR-GFP were incubated with GST or GST-tagged SAR1A in the presence of GDP or GTPγS. After incubation, EGFR-GFP that bound to SAR1A was analyzed by immunoblotting using an antibody against GFP. It was observed that purified GST-SAR1A but not GST specifically bound EGFR from COS7 cell lysate (FIG. 4A-B). Binding occurred in the presence of GDP but was enhanced by the presence of GTPγS (FIG. 4A-B).

FIGS. 5A-5B. Measurement of the effects of D198A mutation in SAR1A on binding between SAR1A and EGFR. GST or GST-tagged SAR1A wild type (wt) or GST-tagged SAR1A mutant bearing D198A mutation (D198A) were purified from bacteria. COS7 cells were transfected with EGFR-GFP. Day1 after transfection, cells were lysed and the cell lysates containing EGFR-GFP were incubated with GST or GST-tagged SAR1A (wt) or GST-tagged SAR1A (D198A). After incubation, EGFR-GFP that bound to SAR1A was analyzed by immunoblotting using an antibody against GFP. It was observed that D198A mutation in SAR1A caused a severe reduction in binding to EGFR (FIG. 5A-B).

FIGS. 7A-7B. Testing the binding between purified EGFR-GFP and SAR1A. Purified EGFR-GFP was incubated with purified GST or GST-SAR1A(A) (wt) (FIG. 7A) or purified EGFR-GFP was incubated with purified GST or GST-SAR1A (wt) or GST-SAR1A (D198A) (FIG. 7B). After incubation, the bound EGFR-GFP was determined by immunoblotting.

FIGS. 9A-9F. Mutating the KKIK motif (SEQ ID NO: 5) on EGFR blocks ER export of EGFR. HeLa cells were transfected with EGFR-GFP (wt) (FIG. 9A-C) and EGFR-GFP (4713-716) (FIG. 9D-F). Day 1 after transfection, the localizations of EGFR and the ER marker, PDI, were analyzed by immunofluorescence. Size bar, 10 μm. It was observed that depleting the KKIK motif (SEQ ID NO: 5) (A 713-716) causes a strong block of EGFR at the ER.

FIGS. 10A-10C. Mutating the Arginine motif in the position of 669-681 of human EGFR affects ER export of EGFR. FIG. 10A. Diagram demonstrating the RUSH transport assay. Cells were transfected with a plasmid construct expressing the streptavidin binding protein (SBP) tagged-reporter protein (SBP-EGFP-reporter), and streptavidin-tagged KDEL (SEQ ID NO: 6) (Str-KDEL (SEQ ID NO: 6)), which is a ER retention motif. Due to the binding between Streptavidin and SBP, SBP-EGFP-reporter will be retained at the ER. When cells were incubated with biotin, SBP-EGFP-reporter will be released from the ER as the SBP tagged of the GFP-reporter will be released from streptavidin-KDEL (SEQ ID NO: 6) by biotin. This strategy serves to synchronize SBP-EGFP-reporters on the way to their destinations along the secretory transport pathway. FIG. 10B. HeLa cells were co-transfected by plasmids expressing Str-KDEL (SEQ ID NO: 6) and SBP-EGFP-EGFR$^{wt}$ or co-transfected by plasmids expressing Str-KDEL (SEQ ID NO: 6) and SBP-EGFP-EGFR$^{\Delta 669\text{-}671}$ and treated as described as the schematic diagram (lower panel). After fixation at the indicated time points, cells expressing the GFP signal were visualized by fluorescent microscope. FIG.

Figure 1:
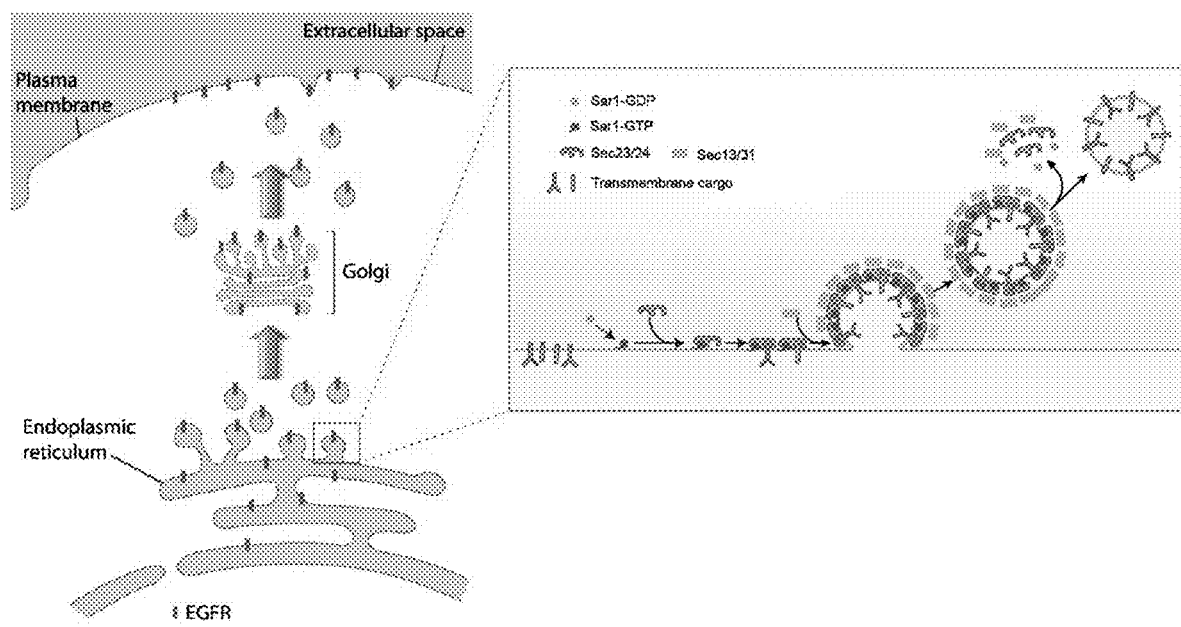
FIG. 1. Surface delivery of newly synthesized EGFR along the secretory transport pathway.

10C. the percentage of cells showing juxtanuclear accumulated-EGFR was quantified (N=3, mean±SD).

FIGS. 11A-11H. Blocking surface delivery of EGFR blocks EGF-induced phosphorylation of EGFR. HeLa cells were transfected with EGFR-GFP or co-transfected with EGFR-GFP and Sar1 (H79G)-DsRed. Day 1 after transfection, cells were treated with EGF and stained with antibodies against phosphorylated EGFR.

DEFINITIONS

A "condition involving excessive or aberrant EGFR signaling" is one caused or exacerbated by an abnormally activated EGFR-mediated cellular signaling response, where EGFR may be over-expressed, or may be inappropriately activated (e.g., continuously activated) such as due to one or more mutations including insertions, deletions, or substitutions in its coding sequence. Conditions involving excessive or aberrant EGFR signaling include EGFR$^+$ cancers such as EGFR$^+$ breast cancer, lung cancer, and ovarian cancer as well as chronic lung diseases such as asthma, bronchiectasis, pulmonary fibrosis, chronic obstructive pulmonary disease (COPD), etc.

"EGFR" or ErbB-1 is a member of the epidermal growth factor (EGF) receptor family of four closely related receptor tyrosine kinases, the others being HER2/neu (ErbB-2), Her 3 (ErbB-3), and Her 4 (ErbB-4). As used herein, "EGFR" includes its human version (e.g., the 1210-amino acid sequence set forth in SEQ ID NO:1 and UniProtKB/Swiss-Prot: P00533), its polymorphic variants and species orthologs or homologs. In this application, an "EGFR polypeptide" refers to a polypeptide comprising an EGFR-derived amino acid sequence, which may be a fragment of the wild-type EGFR sequence (for instance, a portion of EGFR at least about 10, 20, 30, 40, 50, 75, 100, 150, or 200 amino acids in length but less than full-length EGFR, e.g., SEQ ID NO:2) and up to the full-length EGFR amino acid sequence, optionally further comprising one or more heterologous peptide sequence at the N- and/or C-terminus of the EGFR-derived amino acid sequence. For example, an EGFR polypeptide may be a fragment of (less than) full length EGFR encompassing the 669-671 RRR motif and the 713-716 KKIK motif (SEQ ID NO: 5) plus about additional 10, 20, 30, 40, 50, or 75 amino acid residues before residue 669 and/or after residue 716. An "EGFR polynucleotide" refers to a nucleic acid sequence from the gene encoding the EGFR protein and may include both the coding and non-coding regions. "EGFR cDNA," "EGFR mRNA," "EGFR coding sequence," and their variations refer to a nucleic acid sequence that encodes an EGFR polypeptide.

"SAR1A" is a monomeric small GTPase, a subunit found in the coat protein complex II (COPII) vesicles, which are involved in membrane trafficking. As used herein, "SAR1A" includes its human version (e.g., the 198-amino acid sequence set forth in SEQ ID NO:3 and UniProtKB/Swiss-Prot: Q9NR31), its polymorphic variants and species orthologs or homologs. In this application, an "SAR1A polypeptide" refers to a polypeptide comprising an SAR1A-derived amino acid sequence, which may be a fragment of the native SAR1A sequence (for instance, a portion of SAR1A at least about 10, 20, 30, 40, 50, 75, 100, 150, or 170 amino acids in length but less than full-length SAR1A, e.g., SEQ ID NO:4) and up to the full-length SAR1A amino acid sequence, optionally further comprising one or more heterologous peptide sequence at the N- and/or C-terminus of the SAR1A-derived amino acid sequence. For example, an SAR1A polypeptide may be a fragment of (less than) full length SAR1A encompassing residue D198 plus about additional 10, 20, 30, 40, 50, or 75 amino acid residues from before and/or after residue 198. An "SAR1A polynucleotide" refers to a nucleic acid sequence from the gene encoding the SAR1A protein and may include both the coding and non-coding regions. "SAR1A cDNA," "SAR1A mRNA," "SAR1A coding sequence," and their variations refer to a nucleic acid sequence that encodes an SAR1A polypeptide.

As used herein, a "heterologous" polypeptide or nucleotide sequence in the context of a fusion protein or fusion polynucleotide sequence refers to a polypeptide or nucleotide sequence that is not derived from the same origin as its fusion partner. A heterologous peptide in an EGFR polypeptide or an SAR1A polypeptide is from an origin other than EGFR or SAR1A (i.e., not a portion of the EGFR or SAR1A protein sequence), respectively. Frequently, one or more heterologous peptide sequences are included for ease in purification or identification. For example, a heterologous peptide may be any one of the "tags" known and used in the field of recombinant proteins: a peptide tag such as an AviTag, a peptide allowing biotinylation by the enzyme BirA and so the protein can be isolated by streptavidin (GLNDIFEAQKIEWHE (SEQ ID NO: 7)), a Calmodulin-tag, a peptide bound by the protein calmodulin (KRRWKKNFIAVSAANRFKKISSSGAL (SEQ ID NO: 8)), a polyglutamate tag, a peptide binding efficiently to anion-exchange resin such as Mono-Q (EEEEEE (SEQ ID NO: 9)), an E-tag, a peptide recognized by an antibody (GAPVPYPDPLEPR (SEQ ID NO: 10)), a FLAG-tag, a peptide recognized by an antibody (DYKDDDDK (SEQ ID NO: 11)), an HA-tag, a peptide recognized by an antibody (YPYDVPDYA (SEQ ID NO: 12)), a His-tag, 5-10 histidines (SEQ ID NO: 13) bound by a nickel or cobalt chelate (typically 6×His or HHHHHH (SEQ ID NO: 14)), a Myc-tag, a short peptide recognized by an antibody (EQKLISEEDL (SEQ ID NO: 15)), an S-tag (KETAAAKFERQHMDS (SEQ ID NO: 16)), an SBP-tag, a peptide that specifically binds to streptavidin (MDEKTTGWRGGHVVEGLAGELEQLRARLEHHPQGQREP (SEQ ID NO: 17)), a Softag 1 for mammalian expression (SLAELLNAGLGGS (SEQ ID NO: 18)), a Softag 3 for prokaryotic expression (TQDPSRVG (SEQ ID NO: 19)), a Strep-tag, a peptide that binds to streptavidin or the modified streptavidin called streptactin (Strep-tag II: WSHPQFEK (SEQ ID NO: 20)), a TC tag, a tetracysteine tag that is recognized by FlAsH and ReAsH biarsenical compounds (CCPGCC (SEQ ID NO: 21)), a V5 tag, a peptide recognized by an antibody (GKPIPNPLLGLDST (SEQ ID NO: 22)), a VSV-tag, a peptide recognized by an antibody (YTDIEMNRLGK (SEQ ID NO: 23)), an Xpress tag (DLYDDDDK (SEQ ID NO: 24)); or a covalent peptide tags such as an Isopeptag, a peptide that binds covalently to pilin-C protein (TDKDMTITFTNKKDAE (SEQ ID NO: 25)), a SpyTag, a peptide that binds covalently to SpyCatcher protein (AHIVMVDAYKPTK (SEQ ID NO: 26)); or a protein tag such as a BCCP tag (Biotin Carboxyl Carrier Protein), a protein domain biotinylated by BirA enabling recognition by streptavidin, a Glutathione-S-transferase (GST) tag, a protein that binds to immobilized glutathione, a Green fluorescent protein (GFP) tag, a protein that is spontaneously fluorescent and can be bound by nanobodies, a Maltose binding protein (MBP) tag, a protein that binds to amylose agarose, a Nus-tag, a Thioredoxin-tag, an Fc-tag, derived from immunoglobulin Fc domain, allow dimerization and solubilization and can be used for purification on Protein-A Sepharose; as well as other types of tags such as the Ty tag "Inhibitors" or "suppressors" of EGFR-SAR1A binding refer to compounds that have an inhibitory or disruptive effect on the specific binding between EGFR and SAR1A, as identified in in vitro and in vivo binding assays described herein. In some cases, an inhibitor directly binds to either EGFR or SAR1A such that specific binding between EGFR and SAR1A is suppressed or abolished. For instance, a polypeptide such as an EGFR fragment (e.g., SEQ ID NO:2) that specifically binds SAR1A may serve as an inhibitor. An exemplary EGFR polypeptide as an inhibitor is a peptide comprising or consisting of the amino acid sequence set forth in SEQ ID NO:2 and the peptide can be linear or cyclic, or it may be subject to further modification such as glycosylation, PEGylation etc. Similarly, a fragment of SAR1A that specifically binds EGFR may serve an inhibitor of EGFR-SAR1A binding. An exemplary SAR1A polypeptide as an inhibitor is a peptide comprising or consisting of the amino acid sequence set forth in SEQ ID NO:4. The EGFR or SAR1A polypeptide may optionally further include one or more heterologous amino acid sequence located at the N-terminus and/or C-terminus of the EGFR or SAR1A-derived peptide. Inhibitors also include compounds such as small molecules that are capable of reducing or eliminating the binding between EGFR and SAR1A. Assays for inhibitors of EGFR-SAR1A binding include, e.g., applying putative inhibitor compounds to a cell expressing an EGFR polypeptide and an SAR1A polypeptide under conditions that permit EGFR and SAR1A binding and then determining the effect of the compounds on the binding, as described herein. Assays for the inhibitors also include cell-free systems, where samples comprising an EGFR polypeptide and an SAR1A polypeptide treated with a candidate inhibitor are compared to a control sample without the inhibitor to examine the extent of inhibition on the EGFR-SAR1A binding. Control samples (not treated with inhibitors) are assigned a relative binding level of 100%. Inhibition of binding is achieved when the level of binding is undetectable or relative to the control binding level is about 90%, 80%, 70%, 50%, 20%, 10% or close to 0%.

A composition "consisting essentially of an EGFR-SAR1A binding inhibitor" is one that includes an inhibitor of specific binding between EGFR and SAR1A but no other compounds that contribute significantly to the inhibition of the binding. Such compounds may include inactive excipients, e.g., for formulation or stability of a pharmaceutical composition, or active ingredients that do not significantly contribute to the inhibition of EGFR-SAR1A binding. Exemplary compounds consisting essentially of an EGFR-SAR1A inhibitor include therapeutics, medicaments, and pharmaceutical compositions.

As used herein, an "effective amount" or a "therapeutically effective amount" means the amount of a compound that, when administered to a subject or patient for treating a disorder, is sufficient to prevent, reduce the frequency of, or alleviate the symptoms of the disorder. The effective amount will vary depending on a variety of the factors, such as a particular compound used, the disease and its severity, the age, weight, and other factors of the subject to be treated. Amelioration of a symptom of a particular condition by administration of a pharmaceutical composition described herein refers to any lessening, whether permanent or temporary, that can be associated with the administration of the pharmaceutical composition. For example, the amount of an inhibitor of EGFR-SAR1A binding is considered therapeutically effective for treating a condition involving excessive or aberrant EGFR-mediated cellular signaling when treatment results in eliminated symptoms, delayed onset of the symptoms, or reduced frequency or severity of the symptoms.

A "subject," or "subject in need of treatment," as used herein, refers to an individual who seeks medical attention due to risk of, or actual sufferance from, a condition involving excessive or aberrant EGFR-mediated cellular signaling. The term subject can include both animals and humans of any gender or age. Subjects or individuals in need of treatment include those that demonstrate symptoms of a condition involving excessive or aberrant EGFR-mediated cellular signaling (such as an $EGFR^+$ cancer or chronic respiratory disease) or are at risk of later developing these symptoms.

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); and Cassol et al., (1992); Rossolini et al., *Mol. Cell. Probes*, 8:91-98 (1994)). The terms nucleic acid and polynucleotide are used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. An "amino acid" may be either an L- or D-amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "recombinant" when used with reference, e.g., to a cell, or a nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "label," "detectable label," or "detectable moiety" is a composition detectable by radiological, spectroscopic, photochemical, biochemical, immunochemical, chemical, or other physical means. For example, useful labels include radioisotopes such as $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into a polypeptide or used to detect antibodies specifically reactive with the polypeptide. Typically a detectable label is a heterologous moiety attached to a probe or a molecule (e.g., a protein or nucleic acid) with defined binding characteristics (e.g., a polypeptide with a known binding specificity or a polynucleotide), so as to allow the presence of the probe/molecule (and therefore its binding target) to be readily detectable. The heterologous nature of the label ensures that it has an origin different from that of the probe or molecule that it labels, such that the probe/molecule attached with the detectable label does not constitute a naturally occurring composition.

As used in this application, an "increase" or a "decrease" refers to a detectable positive or negative change in quantity from a comparison control, e.g., an established standard control (such as an expression level of EGFR or SAR1A mRNA or protein). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

The term "inhibiting" or "inhibition," as used herein, refers to any detectable negative effect on a target biological process, such as protein phosphorylation, cellular signal transduction, protein synthesis, cell proliferation, tumorigenicity, and metastatic potential etc. Typically, an inhibition is reflected in a decrease of at least 10%, 20%, 30%, 40%, or 50% in target process (e.g., EGFR expression or EGFR-mediated cellular signaling as indicated by phosphorylation of a downstream effector), or any one of the downstream parameters mentioned above, when compared to a control. In a similar fashion, the term "increasing" or "increase" is used to describe any detectable positive effect on a target process, such as a positive change of at least 25%, 50%, 75%, 100%, or as high as 2, 3, 4, 5 or up to 10 or 20 fold, when compared to a control; whereas the term "decreasing" or "decrease" is used to described any detectable negative effect on a target process, such as a negative change of at least 10%, 20%, 25%, 30%, 40%, 50%, 75%, 80%, 90% or more, when compared to a control.

As used herein, the term "specific" describes a process that is selective to a pre-determined molecule or biological process. Typically, the effect of a specific reaction (such as a specific binding or specific inhibition) will be at least twice of the corresponding non-specific effect or the background signal or noise, and preferably more than 10 to 100 times of the background signal.

The term "about" denotes a range of +/−10% of a pre-determined value. For example, "about 10" sets a range of 90% to 110% of 10, i.e., 9 to 11.

DETAILED DESCRIPTION OF THE INVENTION

I. Introduction

During its biosynthesis, EGFR has to be delivered to the cell surface to receive its ligands. The present inventors discovered that blocking the surface delivery of EGFR blocks the ligand-induced EGFR phosphorylation, indicating that blocking surface delivery of EGFR is an effective way to inhibits EGFR signaling and that this strategy can provide a new and effective therapeutic strategy to overcome resistance that cancer patients tend to develop overtime when receiving the currently available EGFR antagonist therapy. A key player in the surface delivery process is the COPII coat. COPII is a type of vesicle coat protein that transports proteins from the rough endoplasmic reticulum to the Golgi apparatus. "COPII" refers to the specific coat protein complex that initiates the budding process. The coat consists of large protein subcomplexes that are made of four different protein subunits, including SAR1A. COPII interacts with specific sorting motifs on cargo proteins, and this interaction is essential to enrich cargo proteins into transport vesicles for surface delivery. The inventors discovered that surface delivery of EGFR depends on the COPII coat subunit, SAR1A. The D198 residue in SAR1A is critical for surface delivery of EGFR. In addition, the KKIK motif (SEQ ID NO: 5) at the position of 713-716 on human EGFR and the arginine residues at the position of 669-671 on human EGFR are important for its ER export. The interaction between COPII subunit SAR1A and EGFR thus serves as a therapeutic target: a compound that can effectively disrupt the binding between EGFR and SAR1A can serve as an effective inhibitor of EGFR signaling thereby inhibiting progression of cancer or other diseases caused or exacerbated by EGFR signaling. These findings allows for one to devise a screening assay to identify novel inhibitors of EGFR signaling, which will be useful in many therapeutic applications.

II. Recombinant Expression of Polypeptides

A. General Recombinant Technology

Basic texts disclosing general methods and techniques in the field of recombinant genetics include Sambrook and Russell, *Molecular Cloning, A Laboratory Manual* (3rd ed.

2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a gene of interest, a polynucleotide encoding a polypeptide of interest, and synthetic oligonucleotides can be verified after cloning or subcloning using, e.g., the chain termination method for sequencing double-stranded templates of Wallace et al., *Gene* 16: 21-26 (1981).

Upon acquiring a polynucleotide sequence encoding EGFR or SAR1A or a fragment of EGFR or SAR1A, the sequence can then be subcloned into a vector, for instance, an expression vector, so that a recombinant polypeptide (e.g., an EGFR or SAR1A polypeptide) can be produced from the resulting construct. Further modifications to the coding sequence, e.g., nucleotide substitutions or codon optimization, may be subsequently made, which may or may not alter the characteristics of the polypeptide.

B. Chemical Synthesis of Polypeptides

The amino acid sequences of human EGFR and SAR1A have been established (e.g., amino acid sequence set forth in SEQ ID NO:1 or 3, corresponding to UniProtKB/Swiss-Prot: P00533.2 or UniProtKB/Swiss-Prot: Q9NR31.1, respectively). Polypeptides of known sequences, especially those of relatively short length such as an EGFR or SAR1A fragment, may be synthesized by solid-phase peptide synthesis methods using procedures similar to those described by Merrifield et al., *J. Am. Chem. Soc.*, 85:2149-2156 (1963); Barany and Merrifield, *Solid-Phase Peptide Synthesis, in The Peptides: Analysis, Synthesis, Biology* Gross and Meienhofer (eds.), Academic Press, N.Y., vol. 2, pp. 3-284 (1980); and Stewart et al., *Solid Phase Peptide Synthesis* 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton et al., *Solid Phase Peptide Synthesis: A Practical Approach*, IRL Press (1989), and Bodanszky, *Peptide Chemistry, A Practical Textbook*, 2nd Ed., Springer-Verlag (1993)).

III. Expression and Purification of Recombinant Polypeptides

Following verification of the coding sequence, a polypeptide of interest (e.g., an EGFR or SAR1A polypeptide) can be produced using routine techniques in the field of recombinant genetics, relying on the polynucleotide sequences encoding the polypeptide disclosed herein.

A. Expression Systems

To obtain high level expression of a nucleic acid encoding a polypeptide of interest, one typically subclones the polynucleotide coding sequence into an expression vector that contains a strong promoter to direct transcription, a transcription/translation terminator and a ribosome binding site for translational initiation. Suitable bacterial promoters are well known in the art and described, e.g., in Sambrook and Russell, supra, and Ausubel et al., supra. Bacterial expression systems for expressing the EGFR or SAR1A polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the desired polypeptide in host cells. A typical expression cassette thus contains a promoter operably linked to the nucleic acid sequence encoding the polypeptide and signals required for efficient polyadenylation of the transcript, ribosome binding sites, and translation termination. The nucleic acid sequence encoding the desired polypeptide is typically linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of *Heliothis virescens*. If, however, a recombinant polypeptide (such as an EGFR or SAR1A polypeptide) is intended to be expressed on the host cell surface, an appropriate anchoring sequence is used in concert with the coding sequence. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the desired polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., an EGFR or SAR1A polypeptide) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

B. Transfection Methods

Standard transfection methods are used to produce bacterial, mammalian, yeast, insect, or plant cell lines that express large quantities of a recombinant polypeptide, which are then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant polypeptide.

C. Purification of Recombinantly Produced Polypeptides

Once the expression of a recombinant polypeptide in transfected host cells is confirmed, e.g., by an immunological assay, the host cells are then cultured in an appropriate scale for the purpose of purifying the recombinant polypeptide.

1. Purification of Recombinantly Produced Polypeptide from Bacteria

When desired polypeptides are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, N.Y.). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer.

Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., Protein Expression and Purification 18: 182-190 (2000).

Alternatively, it is possible to purify recombinant polypeptides from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide is expressed in host cells in a soluble form, its purification can follow the standard protein purification procedure described below. This standard purification procedure is also suitable for purifying polypeptides obtained from chemical synthesis (e.g., an EGFR or SAR1A polypeptide).

i. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., an EGFR or SAR1A polypeptide. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The polypeptides of interest (such as an EGFR or SAR1A polypeptide) can also be separated from other proteins on the basis of their size, net surface charge, hydrophobicity, or affinity for ligands. In addition, antibodies raised against an EGFR or SAR1A polypeptide or binding partners specifically recognizing a heterologous peptide within the EGFR or SAR1A polypeptide can be conjugated to column matrices and the corresponding polypeptide immunopurified. All of these methods are well known in the art.

It will be apparent to one of skill that chromatographic techniques can be performed at any scale and using equipment from many different manufacturers (e.g., Pharmacia Biotech).

VI. Inhibitors of EGFR and SAR1A Binding

A. Inhibitory Nucleic Acids

Inhibition of EGFR or SAR1A gene expression can be achieved through the use of inhibitory nucleic acids. Inhibitory nucleic acids can be single-stranded nucleic acids or oligonucleotides that can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids. In addition, inhibition of EGFR-SAR1A binding can be achieved by administration of a nucleic acid encoding and directing the expression of an EGFR (or SAR1A) fragment that can out-compete the native EGFR (or SAR1A) for specific binding with native SAR1A (or EGFR).

In one embodiment, the inhibitory nucleic acid can specifically bind to a target EGFR or SAR1A polynucleotide. Administration of such inhibitory nucleic acids can inhibit undesired EGFR signaling by reducing or eliminating the transport of newly synthesized EGFR. Nucleotide sequences encoding EGFR and SAR1A are known for several species, including the human cDNA. One can derive a suitable inhibitory nucleic acid from the human EGFR or SAR1A gene sequences, and their polymorphic variants or interspecies orthologs/homologs.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of specific genes that operate by different mechanisms. These different types of inhibitory nucleic acid technology are described in Helene and Toulme, *Biochim. Biophys. Acta.,* 1049:99-125 (1990).

Inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme, supra.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The inhibitory nucleic acids are often targeted to mRNA. In this approach, the inhibitory nucleic acids are designed to specifically block translation of the encoded protein. Using this approach, the inhibitory nucleic acid can be used to selectively suppress certain cellular functions by inhibition of translation of mRNA encoding critical proteins. For example, an inhibitory antisense nucleic acid complementary to regions of a target mRNA inhibits protein expression (see, e.g., Wickstrom et al., *Proc. Nat'l. Acad. Sci. USA*, 85:1028-1032 (1988); and Harel-Bellan et al., *Exp. Med.,* 168:2309-2318 (1988)). As described in Helene and Toulme, supra, inhibitory nucleic acids targeting mRNA have been shown to work by several different mechanisms in order to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme, supra.

The inhibitory nucleic acids can also be used to induce chemical inactivation or cleavage of the target genes or mRNA. Chemical inactivation can occur by the induction of crosslinks between the inhibitory nucleic acid and the target nucleic acid within the cell. Alternatively, irreversible photochemical reactions can be induced in the target nucleic acid by means of a photoactive group attached to the inhibitory nucleic acid. Other chemical modifications of the target nucleic acids induced by appropriately derivatized inhibitory nucleic acids may also be used.

Cleavage, and therefore inactivation, of the target nucleic acids can be affected by attaching to the inhibitory nucleic acid a substituent that can be activated to induce cleavage reactions. The substituent can be one that affects either chemical, photochemical or enzymatic cleavage. For example, one can contact an mRNA:antisense oligonucleotide hybrid with a nuclease which digests mRNA:DNA hybrids. Alternatively cleavage can be induced by the use of ribozymes or catalytic RNA. In this approach, the inhibitory nucleic acids would comprise either naturally occurring RNA (ribozymes) or synthetic nucleic acids with catalytic activity.

Inhibitory nucleic acids can also include RNA aptamers, which are short, synthetic oligonucleotide sequences that bind to proteins (see, e.g., Li et al., *Nuc. Acids Res.* (2006), 34:6416-24). They are notable for both high affinity and specificity for the targeted molecule, and have the additional advantage of being smaller than antibodies (usually less than 6 kD). RNA aptamers with a desired specificity are generally selected from a combinatorial library, and can be modified to reduce vulnerability to ribonucleases, using methods known in the art.

Suppression of EGFR or SAR1A expression can be achieved through the use of nucleic acids siRNA, microRNA, miniRNa, lncRNA, antisense oligonucleotides, aptamer and the like as detailed above. Such nucleic acids can be single-stranded nucleic acids (such as mRNA) or double-stranded nucleic acids (such as DNA) that can translate into an active form of inhibitor of EGFR or SAR1A mRNA under appropriate conditions.

In one embodiment, the EGFR or SAR1A inhibitor-encoding nucleic acid is provided in the form of an expression cassette, typically recombinantly produced, having a promoter operably linked to the polynucleotide sequence encoding the inhibitor. In some cases, the promoter is a universal promoter that directs gene expression in all or most tissue types; in other cases, the promoter is one that directs gene expression specifically in epithelial cells, especially in epithelial cancer cells. Administration of such nucleic acids can suppress EGFR or SAR1A expression in the target tissue, e.g., epithelial cells. Since the human EGFR and SAR1A gene sequences encoding their mRNA sequences are known as EGFR (gene ID: EGFR; NCBI Reference Sequence: NM_005228.5) and SAR1A (gene ID: SAR1A; NCBI Reference Sequence: NM_001142648.1) respectively, one can devise a suitable EGFR- or SAR1A-suppressing nucleic acid from the sequence, species homologs, and variants of these sequences.

B. Identification of EGFR and SAR1A Binding Inhibitors

One can identify compounds that are effective inhibitors of EGFR and SAR1A binding by screening a variety of compounds and mixtures of compounds for their ability to suppress the binding between an EGFR polypeptide and an SAR1A polypeptide, each comprising the essential fragment of EGFR and SAR1A, respectively, for EGFR-SAR1A binding. The testing can be performed in a cell-based system or in a cell-free system, using either the full length sequence of EGFR and SAR1A, or a polypeptide comprising a minimal region or subsequence of EGFR (which is sufficient to support the specific binding between EGFR and SAR1A, such as SEQ ID NO:2) and a polypeptide comprising an SAR1A fragment (which is sufficient to support the specific binding between EGFR and SAR1A, such as SEQ ID NO:4).

One aspect of the present invention is directed to methods for screening compounds that have the activity to inhibit the specific binding between EGFR and SAR1A. Such compounds can be in the form of a mixture of suitable inhibitors, or each in substantially isolated form. An example of an in vitro binding assay can comprise an EGFR polypeptide and an SAR1A polypeptide, where the level of specific binding between the EGFR and SAR1A polypeptides is determined in the presence or absence of a test compound. Optionally, one of the EGFR and SAR1A polypeptides is immobilized to a solid substrate or support. A detectable label, e.g., a radioactive or fluorescent label, can be provided for the SAR1A or EGFR polypeptide, either directly or indirectly (through a second molecule that specifically recognizes SAR1A or EGFR), to facilitate detection of EGFR-SAR1A binding.

Another typical binding assay comprises cells expressing an EGFR polypeptide on their surface and a free SAR1A polypeptide, where the level of specific binding between the two polypeptides is determined in the presence or absence of a test compound. Suitable cells include any cultured cells such as mammalian, insect, microbial (e.g., bacterial, yeast, fungal), or plant cells. In some embodiments, the cells recombinantly express the EGFR polypeptide and the free SAR1A polypeptide.

In some embodiments, the assays are designed to screen large chemical libraries by automating the assay steps and providing compounds from any convenient source to assays, which are typically run in parallel (e.g., in microtiter formats on microtiter plates in robotic assays).

In these screening assays it is optional to have positive controls to ensure that the components of the assays are performing properly. For example, a known inhibitor of EGFR and SAR1A binding can be incubated with one sample of the assay, and the resulting change in signal determined according to the methods herein.

Essentially any chemical compound can be tested as a potential inhibitor of EGFR and SAR1A binding by using methods of the present invention. Most preferred are generally compounds that can be dissolved in aqueous or organic (especially DMSO-based) solutions are used. It will be appreciated that there are many suppliers of chemical compounds, such as Sigma (St. Louis, Mo.), Aldrich (St. Louis, Mo.), Sigma-Aldrich (St. Louis, Mo.), and Fluka Chemika-Biochemica Analytika (Buchs, Switzerland).

Inhibitors of EGFR-SAR1A binding can be identified by screening a combinatorial library containing a large number of potential therapeutic compounds (potential modulator compounds). Such "combinatorial chemical libraries" can be screened in one or more assays, as described herein, to identify those library members (particular chemical species or subclasses) that display a desired characteristic activity. The compounds thus identified can serve as conventional "lead compounds" subject to modification and further testing or can be directly used as potential or actual therapeutics.

Preparation and screening of combinatorial chemical libraries are well known to those of skill in the art. Such combinatorial chemical libraries include, but are not limited to, peptide libraries (see, e.g., U.S. Pat. No. 5,010,175; Furka, *Int. J. Pept. Prot. Res.*, 37:487-493 (1991); and Houghton et al., *Nature*, 354:84-88 (1991)) and carbohydrate libraries (see, e.g., Liang et al., *Science*, 274:1520-1522 (1996); and U.S. Pat. No. 5,593,853). Other chemistries for generating chemical diversity libraries can also be used. Such chemistries include, but are not limited to: peptoids (PCT Pub. No. WO 91/19735); encoded peptides (PCT Pub. No. WO 93/20242); random bio-oligomers (PCT Pub. No. WO 92/00091); benzodiazepines (U.S. Pat. No. 5,288,514); diversomers, such as hydantoins, benzodiazepines and dipeptides (Hobbs et al., *Proc. Nat. Acad. Sci. USA*, 90:6909-6913 (1993)); vinylogous polypeptides (Hagihara et al., *J. Amer. Chem. Soc.*, 114:6568 (1992)); nonpeptidal peptidomimetics with β-D-glucose scaffolding (Hirschmann et al., *J. Amer. Chem. Soc.*, 114:9217-9218 (1992)); analogous organic syntheses of small compound libraries (Chen et al., *J. Amer. Chem. Soc.*, 116:2661 (1994)); oligocarbamates (Cho et al., *Science*, 261:1303 (1993)); and/or peptidyl phosphonates (Campbell et al., *J. Org. Chem.*, 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), small organic molecule libraries (see, e.g., benzodiazepines, Baum C&EN, January 18, page 33 (1993); isoprenoids (U.S. Pat. No. 5,569,588); thiazolidinones and metathiazanones (U.S. Pat. No. 5,549,-

974); pyrrolidines (U.S. Pat. Nos. 5,525,735 and 5,519,134); morpholino compounds (U.S. Pat. No. 5,506,337); and benzodiazepines (U.S. Pat. No. 5,288,514)).

Alternatively, one can identify compounds that are suitable inhibitors of EGFR-SAR1A specific binding by screening a variety of compounds and mixtures of compounds for their ability to suppress EGFR or SAR1A mRNA or protein expression. Methods of detecting expression levels are well known in the art, and include both protein- and nucleic acid-based methods.

For example, a test agent can be contacted in vitro with cells expressing EGFR or SAR1A. An agent that inhibits EGFR or SAR1A expression is one that results in a decrease in the level of EGFR or SAR1A polypeptide or transcript, as measured by any appropriate assay common in the art (e.g., Northern blot, RT-PCR, Western blot, or other hybridization or affinity assays), when compared to expression without the test agent. In some embodiments, a test nucleic acid inhibitor can be introduced into a cell, e.g., using standard transfection or transduction techniques, and the level of EGFR or SAR1A expression detected. A typical decrease is a reduction in the expression level by at least 10%, or higher (e.g., at least 20%, 30%, 50%, 75%, 80%, or 90%) compared the level of expression in the absence of the test inhibitor.

Once a test compound is identified in any of the cell-free or cell-cased screening assays as an inhibitor of EGFR-SAR1A binding, the compound may be subject to further testing to confirm its activity in suppressing or abolishing delivery of EGFR to cell surface. For example, cells that express EGFR on their surface can be exposed to or contacted with the compound, preferably in a series of different concentrations, to determine whether EGFR level on the cell surface is decreased in the presence of the compound compared to the EGFR level in the absence of the compound. When a decrease is detected, the compound is confirmed as an inhibitor of EGFR-SAR1A binding and can serve as an effective therapeutic agent for treating diseases or conditions involving excessive or aberrant EGFR signaling such as various types of $EGFR^+$ cancers and chronic lung diseases.

V. Pharmaceutical Compositions and Administration

The present invention also provides pharmaceutical compositions comprising an effective amount of an inhibitor of EGFR-SAR1A binding for inhibiting EGFR signaling, therefore useful in both prophylactic and therapeutic applications designed for various diseases and conditions involving excessive or aberrant EGFR signaling. Pharmaceutical compositions of the invention are suitable for use in a variety of drug delivery systems. Suitable formulations for use in the present invention are found in *Remington's Pharmaceutical Sciences*, Mack Publishing Company, Philadelphia, Pa., 17th ed. (1985). For a brief review of methods for drug delivery, see, Langer, *Science* 249: 1527-1533 (1990).

The pharmaceutical compositions of the present invention can be administered by various routes, e.g., oral, nasal, subcutaneous, transdermal, intramuscular, intravenous, intraperitoneal, or intratumoral. The routes of administering the pharmaceutical compositions include systemic or local delivery to a subject in need thereof at daily doses of about 0.01-5000 mg, preferably 5-500 mg, of an inhibitor of EGFR-SAR1A binding for a 70 kg adult human per day. The appropriate dose may be administered in a single daily dose or as divided doses presented at appropriate intervals, for example as two, three, four, or more subdoses per day.

For preparing pharmaceutical compositions containing an inhibitor of EGFR-SAR1A binding, inert and pharmaceutically acceptable carriers are used. The pharmaceutical carrier can be either solid or liquid. Solid form preparations include, for example, powders, tablets, dispersible granules, capsules, cachets, and suppositories. A solid carrier can be one or more substances that can also act as diluents, flavoring agents, solubilizers, lubricants, suspending agents, binders, or tablet disintegrating agents; it can also be an encapsulating material.

In powders, the carrier is generally a finely divided solid that is in a mixture with the finely divided active component, e.g., an inhibitor of EGFR-SAR1A binding. In tablets, the active ingredient (the inhibitor) is mixed with the carrier having the necessary binding properties in suitable proportions and compacted in the shape and size desired.

For preparing pharmaceutical compositions in the form of suppositories, a low-melting wax such as a mixture of fatty acid glycerides and cocoa butter is first melted and the active ingredient is dispersed therein by, for example, stirring. The molten homogeneous mixture is then poured into convenient-sized molds and allowed to cool and solidify.

Powders and tablets preferably contain between about 5% to about 70% by weight of the active ingredient. Suitable carriers include, for example, magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The pharmaceutical compositions can include the formulation of the active compound of an EGFR-SAR1A binding inhibitor with encapsulating material as a carrier providing a capsule in which the inhibitor (with or without other carriers) is surrounded by the carrier, such that the carrier is thus in association with the compound. In a similar manner, cachets can also be included. Tablets, powders, cachets, and capsules can be used as solid dosage forms suitable for oral administration.

Liquid pharmaceutical compositions include, for example, solutions suitable for oral or parenteral administration, suspensions, and emulsions suitable for oral administration. Sterile water solutions of the active component (e.g., an inhibitor of EGFR-SAR1A binding) or sterile solutions of the active component in solvents comprising water, buffered water, saline, PBS, ethanol, or propylene glycol are examples of liquid compositions suitable for parenteral administration. The compositions may contain pharmaceutically acceptable auxiliary substances as required to approximate physiological conditions, such as pH adjusting and buffering agents, tonicity adjusting agents, wetting agents, detergents, and the like.

Sterile solutions can be prepared by dissolving the active component (e.g., an inhibitor of EGFR-SAR1A binding) in the desired solvent system, and then passing the resulting solution through a membrane filter to sterilize it or, alternatively, by dissolving the sterile compound in a previously sterilized solvent under sterile conditions. The resulting aqueous solutions may be packaged for use as is, or lyophilized, the lyophilized preparation being combined with a sterile aqueous carrier prior to administration. The pH of the preparations typically will be between 3 and 11, more preferably from 5 to 9, and most preferably from 7 to 8.

The pharmaceutical compositions containing the inhibitor can be administered for prophylactic and/or therapeutic treatments. In therapeutic applications, compositions are administered to a patient already suffering from a condition that may be exacerbated by undesirable EGFR signaling in an amount sufficient to prevent, cure, reverse, or at least partially slow or arrest the symptoms of the condition and its complications. An amount adequate to accomplish this is defined as a "therapeutically effective dose." Amounts effective for this use will depend on the severity of the disease or condition and the weight and general state of the patient, but generally range from about 0.1 mg to about 2,000 mg of the inhibitor per day for a 70 kg patient, with dosages of from about 5 mg to about 500 mg of the inhibitor per day for a 70 kg patient being more commonly used.

In prophylactic applications, pharmaceutical compositions containing an inhibitor of EGFR-SAR1A binding are administered to a patient susceptible to or otherwise at risk of developing a disease or condition involving excessive or aberrant EGFR signaling in an amount sufficient to delay or prevent the onset of the symptoms. Such an amount is defined to be a "prophylactically effective dose." In this use, the precise amounts of the inhibitor again depend on the patient's state of health and weight, but generally range from about 0.1 mg to about 2,000 mg of the inhibitor for a 70 kg patient per day, more commonly from about 5 mg to about 500 mg for a 70 kg patient per day.

Single or multiple administrations of the compositions can be carried out with dose levels and pattern being selected by the treating physician. In any event, the pharmaceutical formulations should provide a quantity of a compound sufficient to effectively inhibit the undesirable excessive or aberrant EGFR signaling facilitated by EGFR-SAR1A binding in the patient, either therapeutically or prophylactically.

VI. Therapeutic Applications Using Nucleic Acids

A variety of conditions can be treated by therapeutic approaches that involve introducing into a cell an inhibitory nucleic acid encoding an inhibitor of EGFR-SAR1A binding (e.g., an inhibitory nucleic acid such as antisense or miRNA specifically targeting to suppress EGFR or SAR1A mRNA expression, or a polypeptide fragment of EGFR or SAR1A that outcompetes its corresponding full-length counterpart in EGFR-SAR1A binding) such that the expression of the inhibitor leads to reduced or abolished EGFR-SAR1A binding in the cell. Those amenable to treatment by this approach include a broad spectrum of conditions involving undesirable EGFR-mediated cellular signaling. For discussions on the application of gene therapy towards the treatment of genetic as well as acquired diseases, see, Miller Nature 357:455-460 (1992); and Mulligan Science 260:926-932 (1993).

A. Vectors for Nucleic Acid Delivery

For delivery to a cell or organism, an inhibitory nucleic acid of the invention can be incorporated into a vector. Examples of vectors used for such purposes include expression plasmids capable of directing the expression of the inhibitors in the target cell. In other instances, the vector is a viral vector system wherein the polynucleotide is incorporated into a viral genome that is capable of transfecting the target cell. In a preferred embodiment, the inhibitory nucleic acid can be operably linked to expression and control sequences that can direct transcription of sequence in the desired target host cells. Thus, one can achieve reduced EGFR-SAR1A binding under appropriate conditions in the target cell.

B. Gene Delivery Systems

As used herein, "gene delivery system" refers to any means for the delivery of an inhibitory nucleic acid of the invention to a target cell. Viral vector systems useful in the introduction and expression of an inhibitory nucleic acid include, for example, naturally occurring or recombinant viral vector systems. Depending upon the particular application, suitable viral vectors include replication competent, replication deficient, and conditionally replicating viral vectors. For example, viral vectors can be derived from the genome of human or bovine adenoviruses, vaccinia virus, herpes virus, adeno-associated virus, minute virus of mice (MVM), HIV, sindbis virus, and retroviruses (including but not limited to Rous sarcoma virus), and MoMLV. Typically, the inhibitory nucleic acid is inserted into such vectors to allow packaging of the gene construct, typically with accompanying viral DNA, followed by infection of a sensitive host cell and expression of the gene of interest.

Similarly, viral envelopes used for packaging gene constructs that include the inhibitory nucleic acid can be modified by the addition of receptor ligands or antibodies specific for a receptor to permit receptor-mediated endocytosis into specific cells (see, e.g., WO 93/20221, WO 93/14188, and WO 94/06923).

Retroviral vectors may also be useful for introducing the inhibitory nucleic acid of the invention into target cells or organisms. Retroviral vectors are produced by genetically manipulating retroviruses. The viral genome of retroviruses is RNA. Upon infection, this genomic RNA is reverse transcribed into a DNA copy which is integrated into the chromosomal DNA of transduced cells with a high degree of stability and efficiency. The integrated DNA copy is referred to as a provirus and is inherited by daughter cells as is any other gene. The wild type retroviral genome and the proviral DNA have three genes: the gag, the pol and the env genes, which are flanked by two long terminal repeat (LTR) sequences. The gag gene encodes the internal structural (nucleocapsid) proteins; the pol gene encodes the RNA directed DNA polymerase (reverse transcriptase); and the env gene encodes viral envelope glycoproteins. The 5' and 3' LTRs serve to promote transcription and polyadenylation of virion RNAs. Adjacent to the 5' LTR are sequences necessary for reverse transcription of the genome (the tRNA primer binding site) and for efficient encapsulation of viral RNA into particles (the Psi site) (see, Mulligan, In: *Experimental Manipulation of Gene Expression*, Inouye (ed), 155-173 (1983); Mann et al., *Cell* 33:153-159 (1983); Cone and Mulligan, *Proceedings of the National Academy of Sciences, U.S.A.,* 81:6349-6353 (1984)).

The design of retroviral vectors is well known to those of ordinary skill in the art. In brief, if the sequences necessary for encapsidation (or packaging of retroviral RNA into infectious virions) are missing from the viral genome, the result is a cis acting defect which prevents encapsidation of genomic RNA. However, the resulting mutant is still capable of directing the synthesis of all virion proteins. Retroviral genomes from which these sequences have been deleted, as well as cell lines containing the mutant genome stably integrated into the chromosome are well known in the art and are used to construct retroviral vectors. Preparation of retroviral vectors and their uses are described in many publications including, e.g., European Patent Application EPA 0 178 220; U.S. Pat. No. 4,405,712, Gilboa *Biotechniques* 4:504-512 (1986); Mann et al., *Cell* 33:153-159 (1983); Cone and Mulligan *Proc. Natl. Acad. Sci. USA* 81:6349-6353 (1984); Eglitis et al. *Biotechniques* 6:608-614 (1988); Miller et al. *Biotechniques* 7:981-990 (1989); Miller (1992) supra; Mulligan (1993), supra; and WO 92/07943.

The retroviral vector particles are prepared by recombinantly inserting the desired inhibitory nucleic acid sequence into a retrovirus vector and packaging the vector with retroviral capsid proteins by use of a packaging cell line. The resultant retroviral vector particle is incapable of replication in the host cell but is capable of integrating into the host cell genome as a proviral sequence containing the desired nucleotide sequence. As a result, the patient is capable of producing, for example, the inhibitory nucleic acid, thus eliminating or reducing unwanted EGFR signaling.

Packaging cell lines that are used to prepare the retroviral vector particles are typically recombinant mammalian tissue culture cell lines that produce the necessary viral structural proteins required for packaging, but which are incapable of producing infectious virions. The defective retroviral vectors that are used, on the other hand, lack these structural genes but encode the remaining proteins necessary for packaging. To prepare a packaging cell line, one can construct an infectious clone of a desired retrovirus in which the packaging site has been deleted. Cells comprising this construct will express all structural viral proteins, but the introduced DNA will be incapable of being packaged. Alternatively, packaging cell lines can be produced by transforming a cell line with one or more expression plasmids encoding the appropriate core and envelope proteins. In these cells, the gag, pol, and env genes can be derived from the same or different retroviruses.

A number of packaging cell lines suitable for the present invention are also available in the prior art. Examples of these cell lines include Crip, GPE86, PA317 and PG13 (see Miller et al., *J. Virol.* 65:2220-2224 (1991)). Examples of other packaging cell lines are described in Cone and Mulligan *Proceedings of the National Academy of Sciences, USA,* 81:6349-6353 (1984); Danos and Mulligan *Proceedings of the National Academy of Sciences, USA,* 85:6460-6464 (1988); Eglitis et al. (1988), supra; and Miller (1990), supra.

C. Pharmaceutical Formulations

When used for pharmaceutical purposes, the inhibitory nucleic acid is generally formulated in a suitable buffer, which can be any pharmaceutically acceptable buffer, such as phosphate buffered saline or sodium phosphate/sodium sulfate, Tris buffer, glycine buffer, sterile water, and other buffers known to the ordinarily skilled artisan such as those described by Good et al. *Biochemistry* 5:467 (1966).

The compositions can further include a stabilizer, an enhancer, and/or other pharmaceutically acceptable carriers or vehicles. A pharmaceutically acceptable carrier can contain a physiologically acceptable compound that acts, for example, to stabilize the inhibitory nucleic acids of the invention and any associated vector. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. Examples of carriers, stabilizers or adjuvants can be found in Remington's *Pharmaceutical Sciences,* Mack Publishing Company, Philadelphia, Pa., 17th ed. (1985).

D. Administration of Formulations

The formulations containing an inhibitory nucleic acid can be delivered to any tissue or organ using any delivery method known to the ordinarily skilled artisan. In some embodiments of the invention, the nucleic acid is formulated in mucosal, topical, and/or buccal formulations, particularly mucoadhesive gel and topical gel formulations. Exemplary permeation enhancing compositions, polymer matrices, and mucoadhesive gel preparations for transdermal delivery are disclosed in U.S. Pat. No. 5,346,701.

The formulations containing the inhibitory nucleic acid are typically administered to a cell. The cell can be provided as part of a tissue or as an isolated cell, such as in tissue culture. The cell can be provided in vivo, ex vivo, or in vitro.

The formulations can be introduced into the tissue of interest in vivo or ex vivo by a variety of methods. In some embodiments of the invention, the inhibitory nucleic acid is introduced into cells by such methods as microinjection, calcium phosphate precipitation, liposome fusion, ultrasound, electroporation, or biolistics. In further embodiments, the nucleic acid is taken up directly by the tissue of interest.

In some embodiments of the invention, the inhibitory nucleic acid is administered ex vivo to cells or tissues explanted from a patient, then returned to the patient. Examples of ex vivo administration of therapeutic gene constructs include Nolta et al., *Proc Natl. Acad. Sci. USA* 93(6):2414-9 (1996); Koc et al., *Seminars in Oncology* 23(1):46-65 (1996); Raper et al., *Annals of Surgery* 223(2): 116-26 (1996); Dalesandro et al., *J. Thorac. Cardi. Surg.*, 11(2):416-22 (1996); and Makarov et al., *Proc. Natl. Acad. Sci. USA* 93(1):402-6 (1996).

Effective dosage of the formulations will vary depending on many different factors, including means of administration, target site, physiological state of the patient, and other medicines administered. Thus, treatment dosages will need to be titrated to optimize safety and efficacy. In determining the effective amount of the vector to be administered, the physician should evaluate the particular nucleic acid used, the disease state being diagnosed; the age, weight, and overall condition of the patient, circulating plasma levels, vector toxicities, progression of the disease, and the production of anti-vector antibodies. The size of the dose also will be determined by the existence, nature, and extent of any adverse side-effects that accompany the administration of a particular vector. To practice the present invention, doses ranging from about 10 ng-1 g, 100 ng-100 mg, 1 µg-10 mg, or 30-300 µg inhibitory nucleic acid per patient are typical. Doses generally range between about 0.01 and about 50 mg per kilogram of body weight, preferably between about 0.1 and about 5 mg/kg of body weight or about $10^8$-$10^{10}$ or $10^{12}$ viral particles per injection. In general, the dose equivalent of a naked nucleic acid from a vector is from about 1 µg-100 µg for a typical 70 kg patient, and doses of vectors which include a retroviral particle are calculated to yield an equivalent amount of an inhibitory nucleic acid.

VII. Kits

The invention also provides kits for treating or preventing a condition involving excessive or aberrant EGFR signaling by inhibiting the specific binding between EGFR and SAR1A according to the method of the present invention. The kits typically include a container that contains a pharmaceutical composition having an effective amount of an inhibitor for the specific binding between EGFR and SAR1A, as well as informational material containing instructions on how to dispense the pharmaceutical composition, including description of the type of patients who may be treated (e.g., a person suffering from or at risk of developing a condition involving excessive or aberrant EGFR signaling such as EGFR$^+$ cancer or a chronic lung disease), the schedule (e.g., dose and frequency of administration) and route of administration, and the like. Furthermore, the kit may contain a second container containing at least one therapeutic agent known to be effective for treating cancers, especially cancers originated from epithelial cells, or for treating chronic respiratory diseases such as asthma, COPD, and the like.

EXAMPLES

The following examples are provided by way of illustration only and not by way of limitation. Those of skill in the art will readily recognize a variety of non-critical parameters that could be changed or modified to yield essentially the same or similar results.

Introduction

Epidermal growth factor receptor (EGFR) plays an important role in promoting cancer cell survival. Overexpression of EGFR is observed in the majority of human epithelial cancers and is correlated with poor prognosis. These factors make EGFR one of the major targets for cancer therapy.

Currently, two classes of EGFR antagonists are now in clinical use: anti-EGFR antibodies and small-molecule EGFR tyrosine kinase inhibitors (EGFR TKIs). Anti-EGFR antibodies compete with ligand to bind the extracellular domain of EGFR, and thereby, inhibit ligand-induced EGFR tyrosine kinase activation. EGFR TKIs compete with ATP to bind the intracellular EGFR tyrosine kinase domain and thus inhibit EGFR activation and downstream signaling. EGFR TKIs can effectively block EGFR signaling on tumors that bearing cancer-related mutations on human EGFR but they cannot effectively block EGFR signaling on tumors that overexpressing wild-type EGFR. Moreover, all cancer patients who initially benefit from EGFR-targeted therapies eventually develop resistance within a short period. Thus it is essential to develop a novel strategy to overcome resistance and enhance the efficiency of EGFR-targeted therapies.

One of the major causes for resistance to EGFR-targeted therapy is that tumor cells acquire additional mutations in EGFR that weaken the interaction between EGFR and the drug. Currently except the third generation of EGFR TKIs that target against the T790M mutation on human EGFR, there is no drug that can effectively overcome drug resistance. In addition, currently there are no effective therapies targeting wild-type EGFR in tumors such as head and neck squamous cell carcinoma (HNSCC). To overcome drug resistance it is essential to explore a novel strategy that inhibits the activity of EGFR by an entirely different mechanism. Newly synthesized wild type EGFR has to be delivered to the cell surface in order for EGFR perform its function (FIG. 1). The results of this study indicate that blocking the surface delivery of EGFR is an effective way to inhibit EGFR signaling, and that this method will provide an effective therapeutic strategy to overcome resistance.

Surface delivery of newly synthesized EGFR follows the conventional steps in the secretory transport pathway (FIG. 1). After synthesized from ribosomes, EGFR is firstly translocated in the membrane of the endoplasmic reticulum (ER). After the folding and modification steps at the ER, EGFR is packaged into transport vesicles that are targeted to the Golgi apparatus en route to the cell surface. Newly synthesized EGFR is delivered in transport vesicles from the ER to the Golgi and then from the Golgi to the plasma membrane (inset). COPII coat-mediated packaging of cargo proteins into transport vesicles at the ER. The key player that mediates export of cargo proteins out of the ER is the COPII coat. The COPII coat is composed of five cytosolic proteins:

the small GTPase SAR1, the Sec23/24 heterodimer and the Sec13/31 heterodimer. Assembly of the COPII coat at the ER is initiated by SAR1 which cycles between a GDP-bound state and a GTP-bound state (FIG. 1, inset). The GDP-bound SAR1 is cytosolic. Upon GTP binding, SAR1 undergoes conformational changes in which the N-terminal amphipathic helix is exposed to bind ER membranes. GTP-bound SAR1 recruits the Sec23/24 heterodimer, forming the inner COPII coat. Subsequently, the inner COPII coat recruits the Sec13/31 heterodimer which is thought to polymerize the coat and drive membrane deformation to generate COPII vesicles. In addition to drive vesicle formation, the COPII coat recognizes specific sorting motifs on the cytosolic domain of transmembrane cargo proteins thereby enriching them into budding vesicles (FIG. 1, inset). Disrupt the interaction between COPII and cargo proteins cause defects in ER export and thus blocks surface delivery of a number of cargo proteins. Given its important role in mediating secretion, the COPII coat has been shown to influence cancer cell secretome and regulate metastatic colonization.

Materials and Methods

Cell Culture and Transfection

HeLa, COS7 and HEK 293T cells were maintained in Dulbecco's Modified Eagle Medium (DMEM) containing 10% fetal bovine serum and 1% penicillin streptomycin mix (Invitrogen). DNA plasmids were transfected in HEK 293T cells by polyethylenimine (PEI). For HeLa and COS7 cells, DNA plasmids were transfected using Lipofectamine®2000 (Invitrogen). For transfection of siRNAs, Lipofectamine® 2000 (Invitrogen) was used under suggested protocol.

RUSH Transport Assay

For RUSH (Retention Using Selective Hook) transport assay, HeLa cells were first transfected with plasmid encoding Str-KDEL (SEQ ID NO: 6) and SBP-EGFP-EGFR for 24 hours. To release the SBP-EGFP-EGFR from the ER, cells were treated with 40 μM D-Biotin (Sigma-Aldrich) and 100 ng/μL cycloheximide (Sigma-Aldrich) for the indicated time.

In Vitro Vesicle Formation Assay

For reconstitution of the vesicle budding of EGFR-GFP, HeLa cells were first transfected with plasmids encoding EGFR-GFP, and used for vesicle budding reaction 24 hours after transfection. To set up the in vitro vesicle budding assay, cells were first permeablized in ice cold KOAc buffer (110 mM potassium acetate, 20 mM Hepes, pH.7.2, 2 mM magnesium acetate) containing 4 μg/ml digitonin on ice for 5 mins. These semi-intact cells were then sedimented by centrifugation at 300 g for 3 mins at 4° C. The semi-intact cell pellets were resuspended in high salt KOAc buffer (1M potassium acetate, 20 mM Hepes, pH.7.2, 2 mM magnesium acetate) and incubated on ice for 5 min, followed by washing twice with KOAc buffer and finally resuspended in KOAc buffer. In the budding assay, the semi-intact cells were incubated with reaction mix containing 2 mg/ml rat liver cytosol, 200 μM GTP and an ATP regeneration system (0.5 mM ATP, 0.5 mM UTP, 50 μM GTP, 5 mM creatine phosphate, 25 μg/ml creatine phosphokinase, 0.05 mM EGTA, and 0.5 mM $MgCl_2$) in the presence or absence of other proteins of interest. After incubation at 32° C. for 1 hr, the reaction mixture was centrifuged at 14000 g (medium speed spin) to remove cell debris and large membranes. The supernatant after medium speed spin was then centrifuged at 100,000 g to sediment small vesicles and the pellet fraction was analyzed by immunoblot.

Immunofluorescence and Microscopy

To perform immunofluorescence experiments, cells cultured on 13 mm coverslips were fixed by 4% paraformaldehyde in PBS (137 mM NaCl, 2.7 mM KCl, 10 mM $Na_2HPO_4$, 1.8 mM $KH_2PO_4$, pH 7.4) at room temperature for 20 mins. After fixation, cells were then further permeablized and blocked by blocking buffer (1×PBS containing 0.2 M Glycine, 2.5% FBS and 0.1% Triton X-100) for 30 minutes at room temperature. Primary antibodies diluted by blocking buffer to optimal dilution were added onto coverslips and incubated for 0.5 to 1 hours at room temperature. After incubation with primary antibodies, cells were washed extensively by PBS. Secondary antibodies diluted in blocking buffer were added onto the coverslips and incubated for 0.5 to 1 hour at room temperature, followed by extensive washing by PBS. Finally, coverslips can be mounted on glass slides with cells facing down using ProLong™ Gold Antifade Mountant with DAPI (Invitrogen). Samples were observed under the Zeiss Axio Observer Z1 microscope (Carl Zeiss, Jena, Germany) equipped with an ORCA Flash 4.0 camera (Hamamatsu, Hamamatsu, Japan) and microscopic images were analyzed and processed using Fiji software.

GST Pull Down Assay

COS7 cells were transfected with EGFR-EGFP and cells were harvested and incubated with purified GST protein in the addition of GDP or GTPγS for 3 hours in 4° C. with rotation. After incubation, beads were washed for 3 times with wash buffer (110 mM potassium acetate, 20 mM Hepes, pH.7.2, 2 mM magnesium acetate, 0.5% Triton X-100) and incubated with 2× protein sample buffer (100 mM Tris-HCl pH 6.8, 0.2% Bromophenol Blue, 4% SDS, 20% Glycerol, 25% β-mercaptoethanol) at 55° C. for 30 minutes for western blotting analysis and Ponceau S staining (0.5% (w/v) Ponceau S, 1% acetic acid).

Results

ER Export of EGFR Depends on the Functional SAR1A Subunit of the COPII Coat

The small GTPase SAR1 is a key player in mediating COPII vesicle formation at the ER. Assembly of the COPII coat is initiated by GTP-bound SAR1. And GTP hydrolysis of SAR1 is required for enrichment of cargo proteins into COPII vesicles. SAR1 has two isoforms: SAR1A and SAR1B. Introducing H79G mutation in SAR1A locks SAR1A in its GTP-bound form and inhibits the COPII-dependent ER export process. Here, it was observed that overexpression of SAR1A (H79G)-DsRed in HeLa cells caused strong accumulations of EGFR at the ER (FIG. 2E-H). In contrast, EGFR was localized at the cell surface in HeLa cells not expressing SAR1A (H79G)-DsRed (FIG. 2A-D). This result indicates that ER export of EGFR depends on the functional SAR1A subunit of the COPII coat.

Figure 3:
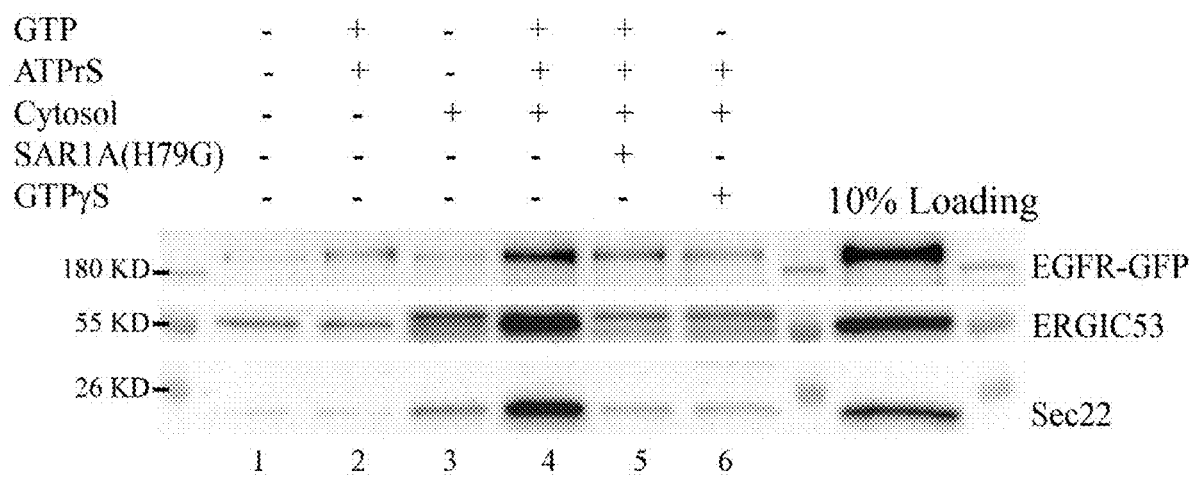
FIG. 3. Examination of the effects of H79G mutation in SAR1A on vesicular release of EGFR. HeLa cells expressing EGFR-GFP were permeablized by digitonin, and then incubated at 30° C. with rat liver cytosol, GTP and an ATP regeneration system in the presence or absence of SAR1A (H79G) mutant. After incubation, the released vesicles were separated from the donor membranes by differentiation centrifugation and were analyzed by immunoblotting with antibodies against ERGIC53, Sec22 and the GFP tag. ERGIC53 and Sec22 are standard COPII cargo proteins and are used as a positive control to monitor COPII vesicular release. Using this assay, cytosol- and nucleotide-dependent vesicular release of EGFR, Sec22 and ERGIC53 was reproducibly detected when permeabilized cells were incubated in the absence of SAR1A (H79G) (FIG. 3, compare lane 4 with lane 1,2,3,6). Remarkably, when the assay was performed in the presence of SAR1A (H79G), a robust reduction of vesicular release of EGFR was observed (FIG. 3, lane 5), indicating that SAR1A plays a direct role in the discharge of EGFR in vesicles.

Next, the inventors sought to reconstitute vesicular release of EGFR from the ER through an in vitro vesicle budding assay. HeLa cells expressing EGFR-GFP were permeabilized by digitonin, and then incubated at 30° C. with rat liver cytosol, GTP and an ATP regeneration system in the presence or absence of SAR1A (H79G) mutant. After incubation, the released vesicles were separated from the donor membranes by differential centrifugation and were analyzed by immunoblotting with antibodies against ERGIC53, Sec22 and the GFP tag. ERGIC53 and Sec22 are standard COPII cargo proteins and are used as a positive control to monitor COPII vesicular release. Using this assay, cytosol- and nucleotide-dependent vesicular release of EGFR, Sec22 and ERGIC53 was repeatedly detected when permeabilized cells were incubated in the absence of SAR1A (H79G) (FIG. 3, compare lane 4 with lane 1,2,3,6). Remarkably, when the assay was performed in the presence of SAR1A (H79G), it was observed a robust reduction of vesicular release of EGFR and the other two cargo proteins (FIG. 3, lane 5), indicating that SAR1A plays a direct role in the discharge of EGFR in vesicles.

EGFR Directly Interacts with the SAR1A Subunit of the COPII Coat

Figure 6:
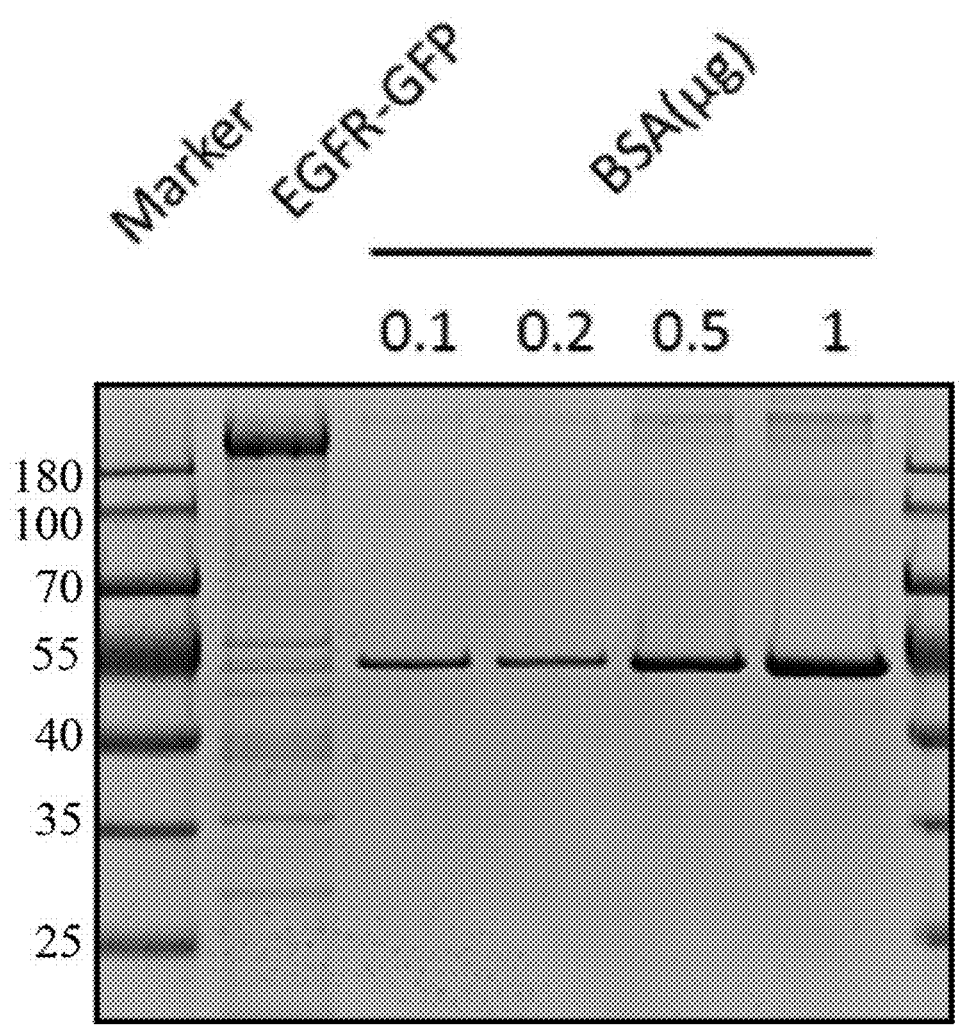
FIG. 6. Purification of EGFR-GFP. COST cells were transfected with EGFR-GFP linked to a biotinated tag through a TEV cleavage site at the C-terminus (EGFR-GFP-BIO). Day1 after transfection, cells were lysed and EGFR-GFP-BIO was pulled down by Streptavidin beads. Subsequently, EGFR-GFP was eluted from the beads by TEV protease and analyzed by SDS-PAGE and coomassie staining (FIG. 6).
Figure 8A:
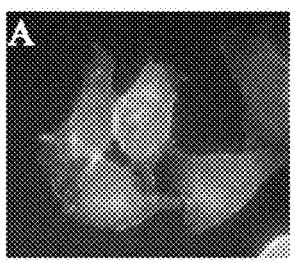
FIGS. 8A-8H. Measurement of the effects of D198A mutation in SAR1A on surface localizations of EGFR. HeLa cells were co-transfected with EGFR-GFP and SAR1A (wt)-DsRed (FIG. 8A-D) or co-transfected with EGFR-GFP and SAR1A (D198A)-DsRed (FIG. 8E-H). Day 1 after transfection, the localizations of EGFR, SAR1A and the ER marker, PDI, were analyzed by immunofluorescence. It was observed that overexpression of SAR1A (D198A)-DsRed but not SAR1A (wt)-DsRed in HeLa cells causes strong accumulations of EGFR at the ER (compare FIG. 8A-D with FIG. 8E-H). Size bar, 10 μm.
Figure 8B:
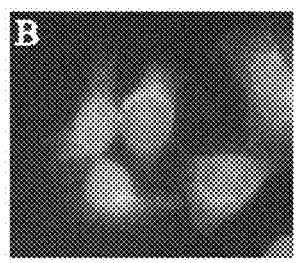
Figure 8C:
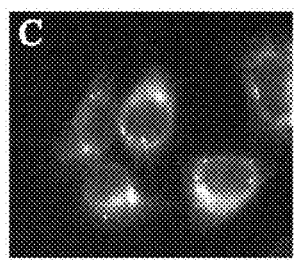
Figure 8D:
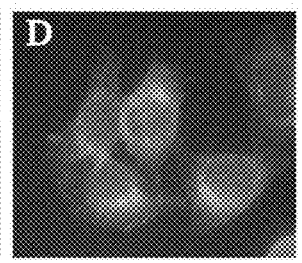
Figure 8E:
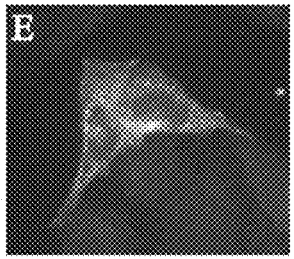
Figure 8F:
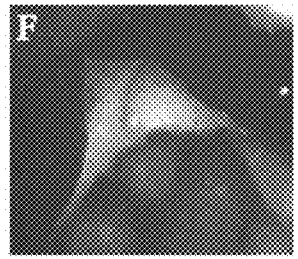
Figure 8G:
Figure 8H:
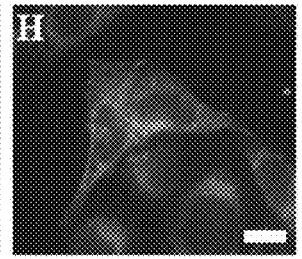
Figure 11A:
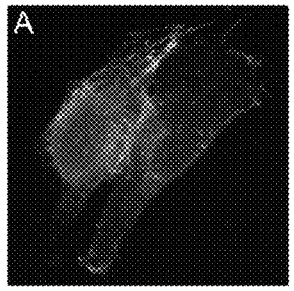
Figure 11B:
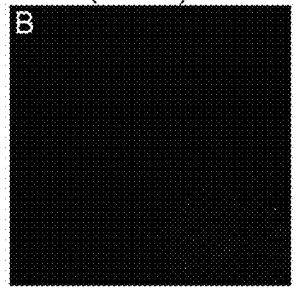
Figure 11C:
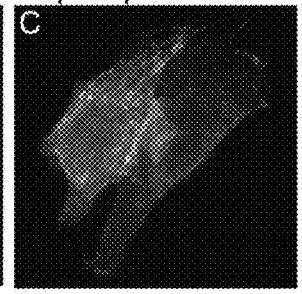
Figure 11D:
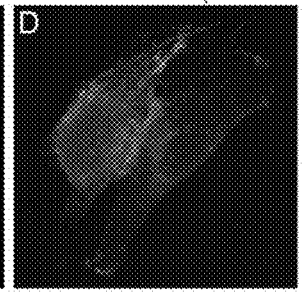
Figure 11E:
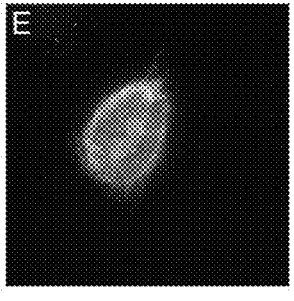
Figure 11F:
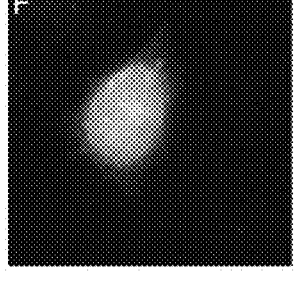
Figure 11G:
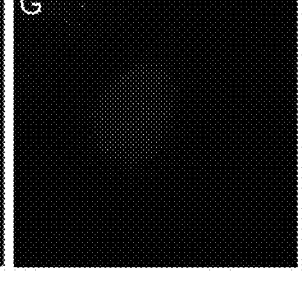
Figure 11H:
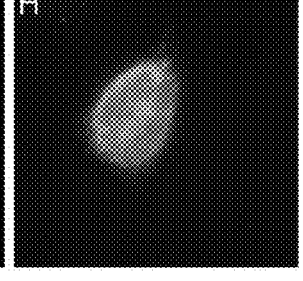

Packaging of cargo proteins into vesicles depends on the interaction between vesicle coat proteins and the cargo molecules (FIG. 1). To test whether EGFR interacts with the COPII coat, GST pull down experiments were performed using purified GST-tagged SAR1A and lysates from COS7 cells expressing EGFR-GFP. Purified GST-SAR1A but not GST specifically bound to EGFR from COS7 cell lysate (FIG. 4A-B). Binding occurred in the presence of GDP but was enhanced by the presence of GTPγS (FIG. 4A-B). SAR1A has been shown to directly interact with the (R/K)X(R/K) motifs in the cytosolic tail of glycosyltransferases and this interaction is reduced by D198A mutation in SAR1A. Similarly, it was observed that D198A mutation in SAR1A caused a severe reduction in binding to EGFR (FIG. 5A-B). EGFR-GFP was then purified from COS7 cells (FIG. 6). Purified EGFR-GFP specifically bound to purified GST-SAR1A but not GST (FIG. 7A), indicating that EGFR directly interacts with the SAR1A subunit of the COPII coat.

D198A mutation in SAR1A reduced the affinity between SAR1A and EGFR (FIG. 7B) suggesting the D198 residue in SAR1A is important for binding between SAR1A and EGFR. Interestingly, overexpression of SAR1A (D198A)-DsRed in HeLa cells caused strong accumulations of EGFR at the ER (FIG. 8E-H). In contrast, EGFR was localized at the cell surface in HeLa cells overexpressing SAR1A (wt)-DsRed (FIG. 8A-D). This result indicates the D198 residue in SAR1A is important for ER export of EGFR.

Human EGFR contains a conserved KKIK motif (SEQ ID NO: 5) at position 713-716. Depletion this motif caused accumulations of EGFR at the ER (FIG. 9). Human EGFR also contains a conserved RRR motif at position 669-671. Mutating this motif did not cause any detectable defects in trafficking of EGFR at steady state. It was then analyzed whether mutating this motif causes defects in kinetic delay of surface delivery of EGFR using RUSH transport assay (FIG. 10A). After biotin release for 40 min, SBP-EGFP-EGFR was transported from ER to the Golgi area in the majority (around 80%) of cells expressing wild type human EGFR (FIG. 10B-C). In contrast, only around 40% of cells expressing the mutant form of EGFR depleted of the RRR motif showed Golgi-localized pattern of EGFR (FIG. 10B-C). The percentage of cells showing Golgi-localized pattern of the mutant version of EGFR (EGFRΔ669-671) was significantly lower than the percentage of cells showing Golgi-localized pattern of wild type EGFR (FIG. 10B-C). This result indicates that the KKIK motif (SEQ ID NO: 5) at position 713-716 and the RRR motif at the position of 669-671 are important for ER export of EGFR.

To test whether blocking ER export of EGFR interferes with EGFR-mediated signaling, HeLa cells were transfected with EGFR-GFP or co-transfected with EGFR-GFP and Sar1 (H79G)-DsRed. Day 1 after transfection, cells were treated with EGF and stained with antibodies against phosphorylated EGFR. Treatment of EGF caused phosphorylation of EGFR detected by the antibodies against phosphorylated EGFR (FIG. 11A-D). Strikingly, overexpressing SAR1A(H79G)-DeRed caused inhibition of EGF-induced phosphorylation of EGFR (FIG. 11E-H). This result indicates that blocking surface delivery of EGFR blocks EGF-induced phosphorylation of EGFR.

Discussions

The present study illustrates that surface delivery of EGFR depends on the COPII coat subunit, SAR1A. In particular, it has been revealed that EGFR directly binds SAR1A. Moreover, the present inventors have identified that the D198 residue in SAR1A is critical for SAR1A to bind EGFR and mutating this residue blocks EGFR surface delivery. In addition, the KKIK motif at the position of 713-716 on human EGFR is important for its ER export. The inventors also discovered that the Arginine residues at the position of 669-671 on human EGFR are important for its ER export. This discovery indicates that, by blocking the interaction between SAR1A and EGFR, one can devise an effective means to inhibit EGFR surface delivery and therefore inhibit EGFR signaling, a strategy that can significantly improve EGFR-targeted therapy. Understanding of this important interaction between EGFR and SAR1A therefore allows for an effective screening assay format one may use to identify inhibitors of this interaction, especially small molecule inhibitors, which can in turn be used for treating conditions and diseases involving excessive or aberrant EGFR signaling such as in various types of EGFR+ cancers and chronic lung diseases.

All patents, patent applications, and other publications cited in this application, including published amino acid or polynucleotide sequences, are incorporated by reference in the entirety for all purposes.

---

INFORMAL SEQUENCE LISTING

SEQ ID NO: 1 amino acid sequence for human EGFR
(UniProtKB/Swiss-Prot: P00533.2)
MRPSGTAGAALLALLAALCPASRALEEKKVCQGTSNKLTQLGTFEDHEL
SLQRMENNCEVVLGNLEITYVQRNYDLSELKTIQEVAGYVLIALNIVER
IPLENLQIIRGNMYYENSYALAVLSNYDANKTGLKELPMRNLQEILHGA
VRESNNPALCNVESIQWRDIVSSDELSNMSMDFQNHLGSCQKCDPSCPN
GSCWGAGEENCQKLTKIICAQQCSGRCRGKSPSDCCHNQCAAGCTGPRE
SDCLVCRKFRDEATCKDTCPPLMLYNPITYQMDVNPEGKYSFGATCVKK
CPRNYVVIDHGSCVRACGADSYEMEEDGVRKCKKCEGPCRKVCNGIGIG
EFKDSLSINATNIKHEKNCTSISGDLHILPVAFRGDSFTHIPPLDPQEL
DILKTVKEITGELLIQAWPENRIDLHAFENLEIIRGRTKQHGQFSLAVV
SLNITSLGLRSLKEISDGDVIISGNKNLCYANTINWKKLFGTSGQKTKI
ISNRGENSCKATGQVCHALCSPEGCWGPEPRDCVSCRNVSRGRECVDKC
NLLEGEPREFVENSECIQCHPECLPQAMNITCTGRGPDNCIQCAHYIDG
PHCVKTCPAGVMGENNTLVWKYADAGHVCHLCHPNCTYGCTGPGLEGCP
INGPKIPSIATGMVGALLLLLVVALGIGLFMRRRHIVRKRTLRRLLQER
ELVEPLIPSGEAPNQALLRILKETEFKKIKVLGSGAFGTVYKGLWIPEG
EKVKIPVAIKELREATSPKANKEILDEAYVMASVDNPHVCRLLGICLTS
TVQLITQLMPFGCLLDYVREHKDNIGSQYLLNWCVQIAKGMNYLEDRRL
VHRDLAARNVLVKTPQHVKITDEGLAKLLGAEEKEYHAEGGKVPIKWMA
LESILHRIYTHQSDVWSYGVTVWELMTFGSKPYDGIPASEISSILEKGE
RLPQPPICTIDVYMIMVKCWMIDADSRPKFRELIIEFSKMARDPQRYLV
IQGDERMHLPSPIDSNEYRALMDEEDMDDVVDADEYLIPQQGFESSPST
SRTPLLSSLSATSNNSTVACIDRNGLQSCPIKEDSFLQRYSSDPTGALT
EDSIDDTFLPVPEYINQSVPKRPAGSVQNPVYHNQPLNPAPSRDPHYQD
PHSTAVGNPEYLNIVQPICVNSTEDSPAHWAQKGSHQISLDNPDYQQDF
FPKEAKPNGIEKGSTAENAEYLRVAPQSSEFIGA SEQ ID NO: 2 EGFR fragment involved in interaction with SAR1A
RRRHIVRKRTLRRLLQERELVEPLIPSGEAPNQALLRILKETEFKKIKV
LGSGAFGTVYKGLWIPEGEKVKIPVAIKELREATSPKANKEILDEAYVM
ASVDNPHVCRLLGICLTSTVQLITQLMPFGCLLDYVREHKDNIGSQYLL
NWCVQIAKGMNYLEDRRLVHRDLAARNVLVKTPQHVKITDEGLAKLLGA
EEKEYHAEGGKVPIKWMALESILHRIYTHQSDVWSYGVTVWELMTEGSK
PYDGIPASEISSILEKGERLPQPPICTIDVYMIMVKCWMIDADSRPKFR
ELIIEFSKMARDPQRYLVIQGDERMHLPSPIDSNEYRALMDEEDMDDVV
DADEYLIPQQGFESSPSTSRTPLLSSLSATSNNSTVACIDRNGLQSCPI
KEDSFLQRYSSDPTGALTEDSIDDTFLPVPEYINQSVPKRPAGSVQNPV
YHNQPLNPAPSRDPHYQDPHSTAVGNPEYLNIVQPICVNSTEDSPAHWA
QKGSHQISLDNPDYQQDFFPKEAKPNGIEKGSTAENAEYLRVAPQSSEF
IGA

INFORMAL SEQUENCE LISTING

SEQ ID NO: 3 amino acid sequence for human SAR1A
(UniProtKB/Swiss-Prot: Q9NR31.1)
MSFIFEWIYNGFSSVLQFLGLYKKSGKLVFLGLDNAGKTTLLHMLKDDR
LGQHVPTLHPTSEELTIAGMTFTTFDLGGHEQARRVWKNYLPAINGIVF
LVDCADHSRLVESKVELNALMTDETISNVPILILGNKIDRTDAISEEKL
REIFGLYGQTTGKGNVTLKELNARPMEVFMCSVLKRQGYGEGFRWLSQY
ID

INFORMAL SEQUENCE LISTING

SEQ ID NO: 4 SAR1A fragment involved in
interaction with EGFR
QFLGLYKKSGKLVFLGLDNAGKTTLLHMLKDDRLGQHVPTLHPTSEELT
IAGMTFTTFDLGGHEQARRVWKNYLPAINGIVFLVDCADHSRLVESKVE
LNALMTDETISNVPILILGNKIDRTDAISEEKLREIFGLYGQTTGKGNV
TLKELNARPMEVFMCSVLKRQGYGEGFRWLSQYID

What is claimed is:

1. A method for identifying an inhibitor for EGFR-SAR1A binding, comprising the steps of:
   (a) contacting a test compound with an EGFR polypeptide comprising the amino acid sequence set forth in SEQ ID NO:2 and an SAR1A polypeptide comprising the amino acid sequence set forth in SEQ ID NO:4, under conditions that permit specific binding between EGFR polypeptide and SAR1A polypeptide; and
   (b) determining the level of specific binding between the EGFR polypeptide and the SAR1A polypeptide, wherein a decrease in the level of specific binding compared to a control level of specific binding between the EGFR polypeptide and the SAR1A polypeptide under the same conditions but in the absence of the test compound indicates the compound as an inhibitor for EGFR-SAR1A binding.

2. The method of claim 1, wherein the EGFR polypeptide comprises the amino acid sequence set forth in SEQ ID NO:1.

3. The method of claim 2, wherein the SAR1A polypeptide comprises the amino acid sequence set forth in SEQ ID NO:3.

4. The method of claim 1, wherein the EGFR polypeptide is immobilized on a solid support.

5. The method of claim 1, wherein the SAR1A polypeptide is immobilized on a solid support.

6. The method of claim 1, wherein the EGFR polypeptide or the SAR1A polypeptide is labeled with a detectable label.

7. The method of claim 1, wherein the EGFR polypeptide further comprises at least one heterologous amino acid sequence at the C- and/or N-terminus of the amino acid sequence set forth in SEQ ID NO:1.

8. The method of claim 1, wherein the EGFR polypeptide further comprises at least one heterologous amino acid sequence at the C- and/or N-terminus of the amino acid sequence set forth in SEQ ID NO:2.

9. The method of claim 1, wherein the SAR1A polypeptide further comprises at least one heterologous amino acid sequence at the C- and/or N-terminus of the amino acid sequence set forth in SEQ ID NO:3.

10. The method of claim 1, wherein the SAR1A polypeptide further comprises at least one heterologous amino acid sequence at the C- and/or N-terminus of the amino acid sequence set forth in SEQ ID NO:4.

11. The method of claim 1, further comprising, after the compound has been identified as an inhibitor for EGFR-SAR1A binding, the steps of (i) exposing a cell expressing EGFR and SAR1A to an effective amount of the compound; and (ii) measuring EGFR-SAR1A binding level in the cell and comparing with EGFR-SAR1A binding level in the absence of the compound or measuring EGFR level on the cell surface and comparing with EGFR level on the cell surface in the absence of the compound.

12. The method of claim 1, wherein the EGFR polypeptide consists of the amino acid sequence set forth in SEQ ID NO:1.

13. The method of claim 1, wherein the EGFR polypeptide consists of the amino acid sequence set forth in SEQ ID NO:2.

14. The method of claim 2, wherein the SAR1A polypeptide consists of the amino acid sequence set forth in SEQ ID NO:3.

15. The method of claim 2, wherein the SAR1A polypeptide consists of the amino acid sequence set forth in SEQ ID NO:4.

* * * * *

SEQUENCE LISTING

<160> NUMBER OF SEQ ID NOS: 26

<210> SEQ ID NO 1
<211> LENGTH: 1210
<212> TYPE: PRT
<213> ORGANISM: Homo sapiens

<400> SEQUENCE: 1

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

-continued

```
Ala Thr Cys Val Lys Lys Cys Pro Arg Asn Tyr Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Cys Glu Gly Pro Cys Arg Lys Val
                325                 330                 335
Cys Asn Gly Ile Gly Ile Gly Glu Phe Lys Asp Ser Leu Ser Ile Asn
                340                 345                 350
Ala Thr Asn Ile Lys His Phe Lys Asn Cys Thr Ser Ile Ser Gly Asp
                355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
                420                 425                 430
His Gly Gln Phe Ser Leu Ala Val Val Ser Leu Asn Ile Thr Ser Leu
            435                 440                 445
Gly Leu Arg Ser Leu Lys Glu Ile Ser Asp Gly Asp Val Ile Ile Ser
        450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
                580                 585                 590
Lys Thr Cys Pro Ala Gly Val Met Gly Glu Asn Asn Thr Leu Val Trp
        595                 600                 605
Lys Tyr Ala Asp Ala Gly His Val Cys His Leu Cys His Pro Asn Cys
        610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
        690                 695                 700
Arg Ile Leu Lys Glu Thr Glu Phe Lys Lys Ile Lys Val Leu Gly Ser
```

-continued

```
        705                 710                 715                 720
Gly Ala Phe Gly Thr Val Tyr Lys Gly Leu Trp Ile Pro Glu Gly Glu
                    725                 730                 735
Lys Val Lys Ile Pro Val Ala Ile Lys Glu Leu Arg Glu Ala Thr Ser
                    740                 745                 750
Pro Lys Ala Asn Lys Glu Ile Leu Asp Glu Ala Tyr Val Met Ala Ser
                    755                 760                 765
Val Asp Asn Pro His Val Cys Arg Leu Leu Gly Ile Cys Leu Thr Ser
770                 775                 780
Thr Val Gln Leu Ile Thr Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                    805                 810                 815
Trp Cys Val Gln Ile Ala Lys Gly Met Asn Tyr Leu Glu Asp Arg Arg
                    820                 825                 830
Leu Val His Arg Asp Leu Ala Ala Arg Asn Val Leu Val Lys Thr Pro
                    835                 840                 845
Gln His Val Lys Ile Thr Asp Phe Gly Leu Ala Lys Leu Leu Gly Ala
                    850                 855                 860
Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                    885                 890                 895
Val Trp Ser Tyr Gly Val Thr Val Trp Glu Leu Met Thr Phe Gly Ser
                    900                 905                 910
Lys Pro Tyr Asp Gly Ile Pro Ala Ser Glu Ile Ser Ser Ile Leu Glu
                    915                 920                 925
Lys Gly Glu Arg Leu Pro Gln Pro Pro Ile Cys Thr Ile Asp Val Tyr
                    930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                    965                 970                 975
Arg Tyr Leu Val Ile Gln Gly Asp Glu Arg Met His Leu Pro Ser Pro
                    980                 985                 990
Thr Asp Ser Asn Phe Tyr Arg Ala  Leu Met Asp Glu Glu  Asp Met Asp
                    995                 1000                1005
Asp Val  Val Asp Ala Asp Glu  Tyr Leu Ile Pro Gln  Gln Gly Phe
    1010                1015                1020
Phe Ser  Ser Pro Ser Thr Ser  Arg Thr Pro Leu Leu  Ser Ser Leu
    1025                1030                1035
Ser Ala  Thr Ser Asn Asn Ser  Thr Val Ala Cys Ile  Asp Arg Asn
    1040                1045                1050
Gly Leu  Gln Ser Cys Pro Ile  Lys Glu Asp Ser Phe  Leu Gln Arg
    1055                1060                1065
Tyr Ser  Ser Asp Pro Thr Gly  Ala Leu Thr Glu Asp  Ser Ile Asp
    1070                1075                1080
Asp Thr  Phe Leu Pro Val Pro  Glu Tyr Ile Asn Gln  Ser Val Pro
    1085                1090                1095
Lys Arg  Pro Ala Gly Ser Val  Gln Asn Pro Val Tyr  His Asn Gln
    1100                1105                1110
Pro Leu  Asn Pro Ala Pro Ser  Arg Asp Pro His Tyr  Gln Asp Pro
    1115                1120                1125
```

-continued

```
His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205                1210

<210> SEQ ID NO 2
<211> LENGTH: 542
<212> TYPE: PRT
<213> ORGANISM: Homo sapiens

<400> SEQUENCE: 2

Arg Arg Arg His Ile Val Arg Lys Arg Thr Leu Arg Arg Leu Leu Gln
1               5                   10                  15

Glu Arg Glu Leu Val Glu Pro Leu Thr Pro Ser Gly Glu Ala Pro Asn
            20                  25                  30

Gln Ala Leu Leu Arg Ile Leu Lys Glu Thr Glu Phe Lys Lys Ile Lys
        35                  40                  45

Val Leu Gly Ser Gly Ala Phe Gly Thr Val Tyr Lys Gly Leu Trp Ile
50                  55                  60

Pro Glu Gly Glu Lys Val Lys Ile Pro Val Ala Ile Lys Glu Leu Arg
65                  70                  75                  80

Glu Ala Thr Ser Pro Lys Ala Asn Lys Glu Ile Leu Asp Glu Ala Tyr
                85                  90                  95

Val Met Ala Ser Val Asp Asn Pro His Val Cys Arg Leu Leu Gly Ile
            100                 105                 110

Cys Leu Thr Ser Thr Val Gln Leu Ile Thr Gln Leu Met Pro Phe Gly
        115                 120                 125

Cys Leu Leu Asp Tyr Val Arg Glu His Lys Asp Asn Ile Gly Ser Gln
    130                 135                 140

Tyr Leu Leu Asn Trp Cys Val Gln Ile Ala Lys Gly Met Asn Tyr Leu
145                 150                 155                 160

Glu Asp Arg Arg Leu Val His Arg Asp Leu Ala Ala Arg Asn Val Leu
                165                 170                 175

Val Lys Thr Pro Gln His Val Lys Ile Thr Asp Phe Gly Leu Ala Lys
            180                 185                 190

Leu Leu Gly Ala Glu Glu Lys Glu Tyr His Ala Glu Gly Gly Lys Val
        195                 200                 205

Pro Ile Lys Trp Met Ala Leu Glu Ser Ile Leu His Arg Ile Tyr Thr
    210                 215                 220

His Gln Ser Asp Val Trp Ser Tyr Gly Val Thr Val Trp Glu Leu Met
225                 230                 235                 240

Thr Phe Gly Ser Lys Pro Tyr Asp Gly Ile Pro Ala Ser Glu Ile Ser
                245                 250                 255

Ser Ile Leu Glu Lys Gly Glu Arg Leu Pro Gln Pro Pro Ile Cys Thr
            260                 265                 270

Ile Asp Val Tyr Met Ile Met Val Lys Cys Trp Met Ile Asp Ala Asp
```

```
                    275                 280                 285
Ser Arg Pro Lys Phe Arg Glu Leu Ile Ile Glu Phe Ser Lys Met Ala
290                 295                 300

Arg Asp Pro Gln Arg Tyr Leu Val Ile Gln Gly Asp Glu Arg Met His
305                 310                 315                 320

Leu Pro Ser Pro Thr Asp Ser Asn Phe Tyr Arg Ala Leu Met Asp Glu
                325                 330                 335

Glu Asp Met Asp Asp Val Val Asp Ala Asp Glu Tyr Leu Ile Pro Gln
            340                 345                 350

Gln Gly Phe Phe Ser Ser Pro Ser Thr Ser Arg Thr Pro Leu Leu Ser
        355                 360                 365

Ser Leu Ser Ala Thr Ser Asn Asn Ser Thr Val Ala Cys Ile Asp Arg
370                 375                 380

Asn Gly Leu Gln Ser Cys Pro Ile Lys Glu Asp Ser Phe Leu Gln Arg
385                 390                 395                 400

Tyr Ser Ser Asp Pro Thr Gly Ala Leu Thr Glu Asp Ser Ile Asp Asp
                405                 410                 415

Thr Phe Leu Pro Val Pro Glu Tyr Ile Asn Gln Ser Val Pro Lys Arg
            420                 425                 430

Pro Ala Gly Ser Val Gln Asn Pro Val Tyr His Asn Gln Pro Leu Asn
        435                 440                 445

Pro Ala Pro Ser Arg Asp Pro His Tyr Gln Asp Pro His Ser Thr Ala
450                 455                 460

Val Gly Asn Pro Glu Tyr Leu Asn Thr Val Gln Pro Thr Cys Val Asn
465                 470                 475                 480

Ser Thr Phe Asp Ser Pro Ala His Trp Ala Gln Lys Gly Ser His Gln
                485                 490                 495

Ile Ser Leu Asp Asn Pro Asp Tyr Gln Gln Asp Phe Phe Pro Lys Glu
            500                 505                 510

Ala Lys Pro Asn Gly Ile Phe Lys Gly Ser Thr Ala Glu Asn Ala Glu
        515                 520                 525

Tyr Leu Arg Val Ala Pro Gln Ser Ser Glu Phe Ile Gly Ala
530                 535                 540

<210> SEQ ID NO 3
<211> LENGTH: 198
<212> TYPE: PRT
<213> ORGANISM: Homo sapiens

<400> SEQUENCE: 3

Met Ser Phe Ile Phe Glu Trp Ile Tyr Asn Gly Phe Ser Ser Val Leu
1               5                   10                  15

Gln Phe Leu Gly Leu Tyr Lys Lys Ser Gly Lys Leu Val Phe Leu Gly
            20                  25                  30

Leu Asp Asn Ala Gly Lys Thr Thr Leu Leu His Met Leu Lys Asp Asp
        35                  40                  45

Arg Leu Gly Gln His Val Pro Thr Leu His Pro Thr Ser Glu Glu Leu
    50                  55                  60

Thr Ile Ala Gly Met Thr Phe Thr Thr Phe Asp Leu Gly Gly His Glu
65                  70                  75                  80

Gln Ala Arg Arg Val Trp Lys Asn Tyr Leu Pro Ala Ile Asn Gly Ile
                85                  90                  95

Val Phe Leu Val Asp Cys Ala Asp His Ser Arg Leu Val Glu Ser Lys
            100                 105                 110
```

Val Glu Leu Asn Ala Leu Met Thr Asp Glu Thr Ile Ser Asn Val Pro
            115                 120                 125

Ile Leu Ile Leu Gly Asn Lys Ile Asp Arg Thr Asp Ala Ile Ser Glu
    130                 135                 140

Glu Lys Leu Arg Glu Ile Phe Gly Leu Tyr Gly Gln Thr Thr Gly Lys
145                 150                 155                 160

Gly Asn Val Thr Leu Lys Glu Leu Asn Ala Arg Pro Met Glu Val Phe
                165                 170                 175

Met Cys Ser Val Leu Lys Arg Gln Gly Tyr Gly Glu Gly Phe Arg Trp
            180                 185                 190

Leu Ser Gln Tyr Ile Asp
        195

<210> SEQ ID NO 4
<211> LENGTH: 182
<212> TYPE: PRT
<213> ORGANISM: Homo sapiens

<400> SEQUENCE: 4

Gln Phe Leu Gly Leu Tyr Lys Lys Ser Gly Lys Leu Val Phe Leu Gly
1               5                   10                  15

Leu Asp Asn Ala Gly Lys Thr Thr Leu Leu His Met Leu Lys Asp Asp
            20                  25                  30

Arg Leu Gly Gln His Val Pro Thr Leu His Pro Thr Ser Glu Glu Leu
        35                  40                  45

Thr Ile Ala Gly Met Thr Phe Thr Thr Phe Asp Leu Gly Gly His Glu
    50                  55                  60

Gln Ala Arg Arg Val Trp Lys Asn Tyr Leu Pro Ala Ile Asn Gly Ile
65                  70                  75                  80

Val Phe Leu Val Asp Cys Ala Asp His Ser Arg Leu Val Glu Ser Lys
                85                  90                  95

Val Glu Leu Asn Ala Leu Met Thr Asp Glu Thr Ile Ser Asn Val Pro
            100                 105                 110

Ile Leu Ile Leu Gly Asn Lys Ile Asp Arg Thr Asp Ala Ile Ser Glu
        115                 120                 125

Glu Lys Leu Arg Glu Ile Phe Gly Leu Tyr Gly Gln Thr Thr Gly Lys
    130                 135                 140

Gly Asn Val Thr Leu Lys Glu Leu Asn Ala Arg Pro Met Glu Val Phe
145                 150                 155                 160

Met Cys Ser Val Leu Lys Arg Gln Gly Tyr Gly Glu Gly Phe Arg Trp
                165                 170                 175

Leu Ser Gln Tyr Ile Asp
            180

<210> SEQ ID NO 5
<211> LENGTH: 4
<212> TYPE: PRT
<213> ORGANISM: Unknown
<220> FEATURE:
<223> OTHER INFORMATION: Description of Unknown: KDEL motif
      peptide

<400> SEQUENCE: 5

Lys Lys Ile Lys
1

<210> SEQ ID NO 6
<211> LENGTH: 4

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Asp Glu Leu
1

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Leu Asn Asp Ile Phe Glu Ala Gln Lys Ile Glu Trp His Glu
1               5                   10                  15

<210> SEQ ID NO 8
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Glu Glu Glu Glu Glu
1               5

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ala Pro Val Pro Tyr Pro Asp Pro Leu Glu Pro Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 11

Asp Tyr Lys Asp Asp Asp Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Tyr Asp Val Pro Asp Tyr Ala
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: MISC_FEATURE
<222> LOCATION: (1)..(10)
<223> OTHER INFORMATION: This sequence may encompass 5-10 residues

<400> SEQUENCE: 13

His His His His His His His His His His
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 14

His His His His His His
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Gln Lys Leu Ile Ser Glu Glu Asp Leu
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys Glu Thr Ala Ala Ala Lys Phe Glu Arg Gln His Met Asp Ser
1               5                   10                  15
```

```
<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Leu Ala Glu Leu Leu Asn Ala Gly Leu Gly Gly Ser
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Gln Asp Pro Ser Arg Val Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Ser His Pro Gln Phe Glu Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Cys Cys Pro Gly Cys Cys
1               5

<210> SEQ ID NO 22
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Lys Pro Ile Pro Asn Pro Leu Leu Gly Leu Asp Ser Thr
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Tyr Thr Asp Ile Glu Met Asn Arg Leu Gly Lys
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asp Leu Tyr Asp Asp Asp Asp Lys
1               5

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Asp Lys Asp Met Thr Ile Thr Phe Thr Asn Lys Lys Asp Ala Glu
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala His Ile Val Met Val Asp Ala Tyr Lys Pro Thr Lys
1               5                   10
```